United States Patent
Persikov et al.

(10) Patent No.: US 8,280,710 B2
(45) Date of Patent: Oct. 2, 2012

(54) METHOD FOR DETERMINING THERMAL STABILITY OF COLLAGEN OR COLLAGEN-LIKE PEPTIDE

(75) Inventors: Anton V. Persikov, Highland Park, NJ (US); John A. M. Ramshaw, Pascoe Vale (AU); Barbara M. Brodsky, Kendall Park, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 895 days.

(21) Appl. No.: 11/814,607

(22) PCT Filed: Feb. 3, 2006

(86) PCT No.: PCT/US2006/003961
§ 371 (c)(1),
(2), (4) Date: Jun. 24, 2008

(87) PCT Pub. No.: WO2006/084189
PCT Pub. Date: Aug. 10, 2006

(65) Prior Publication Data
US 2009/0176971 A1      Jul. 9, 2009

Related U.S. Application Data

(60) Provisional application No. 60/649,736, filed on Feb. 3, 2005.

(51) Int. Cl.
*G06G 7/48* (2006.01)
(52) U.S. Cl. ....................................................... 703/11
(58) Field of Classification Search ...................... 703/11
See application file for complete search history.

(56) References Cited

OTHER PUBLICATIONS

Bachinger et al., "Sequence specific thermal stability of the collagen triple helix", Int. J. Biol. Macromol. 1991 13:152-156.
Bachinger et al., "Thermal Stability and Folding of the Collagen Triple Helix and the Effects of Mutations in Osteogenesis Imperfecta on the Triple Helix of Type I Collagen", American Journal of Medical Genetics 1993 45:152-162.
Buevich et al., "Transformation of the Mechanism of Triple-helix Peptide Folding in the Absence of a C-terminal Nucleation Domain and Its Implications for Mutations in Collagen Disorders", J. Biol. Chem. 279(45):46890-46895.
Chan et al., "Positional Preferences of Ionizable Residues in Gly-X-Y Triplets of the Colagen Triple-helix", J. Biol. Chem. 1997 272(50):31441-31446.
Persikov et al., "Electrostatis Interactions Involving Lysine Make Major Contributions to Collagen Triple-Helix Stability", Biochemistry 2005 44:1414-1422.
Persikov et al., "Peptide Investigations of Pairwise Interactions in the Collagen Triple-helix", J. Mol. Biol. 2002 316:385-394.
Persikov et al., "Triple-Helix Propensity of Hydroxyproline and Fluoroproline:Comparison of Host-Guest and Repeating Tripleptide Collagen Models", J. Am. Chem. Soc. 2003 125:11500-11501.
Persikov et al., "Amino Acid Propensities for the Collagen Triple-Helix", Biochemistry 2000 39:14960-14967.
Persikov et al., "Collagen Model Peptides:Sequence Dependence of Triple-Helix Stability", Biopolymers (Pept Sci) 2000 55:436-450.
Rameshaw, John A.M., "Gly-X-Y Tripetide Frequencies in Collagen:A Context for Host-Guest Triple-Helical Peptides", J. Structural Biology 1998 122:86-91.
Sutoh et al., "Conformational Change of the Triple-Helical Structure. II. Conformation of (Pro-Pro-Gly)n, and (Pro-Pro-Gly)n, (Ala-Pro-Gly)m(Pro-Pro-Gly)n in an Aqueous Solution", Biopolymers 1974 13:2391-2404.
Venugopal et al., "Electrostatis Interactions in Collagen-like Triple-Helical Peptides", Biochemistry 1994 33:7948-7956.

*Primary Examiner* — Jerry Lin
(74) *Attorney, Agent, or Firm* — Licata & Tyrrell P.C.

(57) ABSTRACT

The present invention is a method for determining the thermal stability of a collagen peptide, collagen-like peptide or triple-helix construct with the repeating peptide unit Gly-$Xaa_1$-$Xaa_2$. The instant method accounts for the destabilizing effect of peptide repeats which do not conform to the highly stable Gly-Pro-Hyp peptide and for the interaction between triplets. The instant method finds use in mutant analysis of collagen peptides, collagen-like peptides or triple-helix constructs and engineering of collagen peptides, collagen-like peptides or triple-helix constructs.

4 Claims, 3 Drawing Sheets

GLY-XAA$_1$-XAA$_2$-GLY-XAA$_1$'-XAA$_2$'-GLY-XAA$_1$"-XAA$_2$"

METHOD FOR DETERMINING THERMAL STABILITY OF COLLAGEN OR COLLAGEN-LIKE PEPTIDE

This application claims benefit of U.S. Provisional Patent Application Ser. No. 60/649,736, filed Feb. 3, 2005, the contents of which are incorporated herein by reference in their entirety.

This invention was made in the course of research sponsored by the National Institutes of Health (Grant No. GM60048). The U.S. government may have certain rights in this invention.

INTRODUCTION

Background of the Invention

The ability to predict structure and stability from amino acid sequence is an important step in the understanding of basic protein principles and the structural consequences of pathological mutations. The vast number of amino acid sequences available from DNA data contrasts with the smaller number of high resolution protein structures and the limited experimental data on protein stability. The ability to make predictions that are in good agreement with experimental data provides insight into the stabilizing interactions within proteins. In addition, there is much interest in computing the effect of single amino acid replacements on protein stability because destabilizing effects are associated with deleterious mutations that result in clinically detectable phenotypes (Wang and Moult (2001) *Hum. Mutat.* 17:263-270; Guerois, et al. (2002) *J. Mol. Biol.* 320:369-387; Persikov, et al. (2004) *Hum. Mutat.* 24:330-337). In contrast to globular proteins, the relation among sequence, structure, and stability is simpler and better defined for the linear collagen triple helix.

The collagen triple helix motif is found widely in structural proteins of the extracellular matrix and in an increasing number of non-collagenous proteins, many of which are involved in host-defense functions (Myllyharju and Kivirikko (2004) *Trends Genet.* 20:33-43; Brodsky and Persikov (2005) *Adv. Protein Chem.* 70:301-339). The close packing of three super-coiled polyproline II-like polypeptide chains in the collagen triple helix generates a requirement for Gly as every third residue (Rich and Crick (1961) *J. Mol. Diol.* 3:483-506; Ramachandran (1963) *Int. Rev. Connect. Tissue Res.* 68:127-182; Bella, et al. (1994) *Science* 266:75-81). The observation of such a repeating $(Gly-Xaa_1-Xaa_2)_n$ sequence pattern over a stretch of residues signifies a triple helix conformation. However, the collagen triple helix is not uniform in structure or stability. Crystal structures of collagen peptides show that variation in amino acid content leads to small but significant variations in the super-helix twist (Kramer, et al. (1999) *Nat. Struct. Biol.* 6:454-457; Kramer, et al. (2001) *J. Mol. Biol.* 311:131-147; Emsley, et al. (2004) *J. Mol. Biol.* 335:1019-1028). Calorimetric results suggest the presence of multiple independent folding domains along a collagen molecule (Privalov (1982) *Adv. Protein Chem.* 35:1-104), and the presence of regions of different stability was confirmed by studies on recombinant collagen constructs (Steplewski, et al. (2004) *J. Struct. Biol.* 148:326-337). There are multiple binding domains in collagens (Di Lullo, et al. (200-2) *J. Biol. Chem.* 277:4223-4231), and regions of decreased triple helix stability have been implicated in binding in some cases (Shah, et al. (1997) *Biochemistry* 36:5878-5883; Chung, et al. (2004) *EMBO J.* 23:3020-3030; Deprez, et al. (2000) *Biochem. J.* 350:283-290). Self-association of type I collagen into fibrils is preceded by micro-unfolding of specific triple helix regions (Leikina, et al. (2002) *Proc. Natl. Acad. Sci. USA* 99:1314-1318; Kadler, et al. (1988) *J. Biol. Chem.* 263:10517-10523). Thus, specific residues along the $(Gly-Xaa_1-Xaa_2)_n$ sequence determine functionally important to modulation of structure and stability.

SUMMARY OF THE INVENTION

The present invention is a method for determining the thermal stability of a collagen peptide, collagen-like peptide or triple-helix construct. The method involves the steps of:
 a) identifying the number of consecutive $Gly-Xaa_1-Xaa_2$ amino acid repeats in a collagen peptide, collagen-like peptide or triple-helix construct;
 b) determining the maximum melting temperature of the collagen or collagen-like peptide relative to the melting temperature of a $(Gly-Pro-Hyp)_n$ peptide, wherein n corresponds to the number of consecutive $Gly-Xaa_1-Xaa_2$ amino acid repeats in the collagen peptide, collagen-like peptide or triple-helix construct;
 c) identifying $Gly-Xaa_1-Xaa_2$ amino acid repeats in the collagen peptide, collagen-like peptide or triple-helix construct wherein $Xaa_1$ is not Pro or $Xaa_2$ is not Hyp;
 d) determining the melting temperature of each n repeat of step c) relative to the melting temperature of a Gly-Pro-Hyp peptide;
 e) adjusting the melting temperature of each n repeat of step d) with a reference melting temperature for each n repeat of step d);
 f) combining the adjusted melting temperatures of the n repeats of steps e) so that a correction melting temperature is determined for $Gly-Xaa_1-Xaa_2$ repeats; and
 g) adjusting the maximum melting temperature of the collagen peptide, collagen-like peptide or triple-helix construct of step b) with the correction melting temperature of f) to determine the thermal stability the collagen peptide, collagen-like peptide or triple-helix construct.

In particular embodiments, the instant method further includes the step of: h) identifying the presence of a stabilizing sequence motif in the collagen peptide, collagen-like peptide or triple-helix construct and adjusting the melting temperature of step g) for the collagen peptide, collagen-like peptide or triple-helix construct when the stabilizing sequence motif is present.

In other embodiments, the method of the present invention is used for designing a collagen peptide, collagen-like peptide or triple-helix construct with a predetermined thermal stability that is either increased or decreased compared to a wild-type collagen peptide, collagen-like peptide or triple-helix construct.

In another embodiment, the method of the present invention is applied to determining local thermal stability variations within a full-length collagen protein or collagen domain of a protein, in particular a protein having one or more amino acid substitutes which lead to a disease phenotype.

and (Pro-Pro-Gly)$_n$ (open circle). The $T_m$ values are shown for (Pro-Pro-Gly)$_n$ for n=12, 15, and 20 (c=3 mg/ml, 3% HAc, equilibrium conditions) (Sutoh and Noda (1974) *Biopolymers* 13:2391-2404); for n=10 (Persikov, et al. (2004) *Protein Sci.* 13:893-902); and for n=9. The $T_m$ values for (Pro-Hyp-Gly)$_n$ were obtained using standard melting conditions. The extrapolated curve is shown as a solid line, as described by Equation 3. The two points (solid squares) show the experimental $T_m$ values for the blocked Ac-(Pro-Hyp-Gly)$_n$-NH$_2$ peptides for n=7 and 8.

Figure 3:
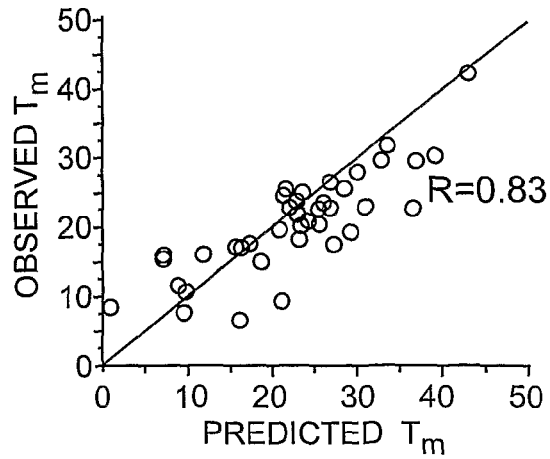
Figure 4A:
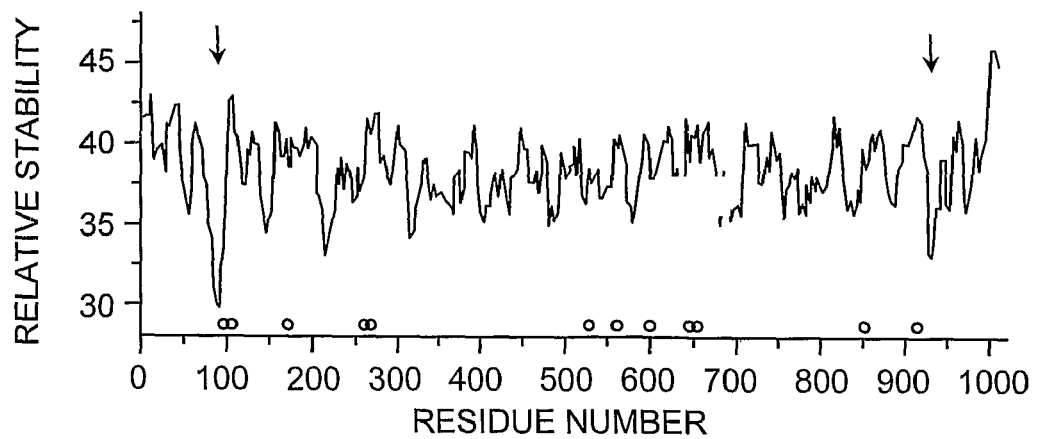
Figure 4B:
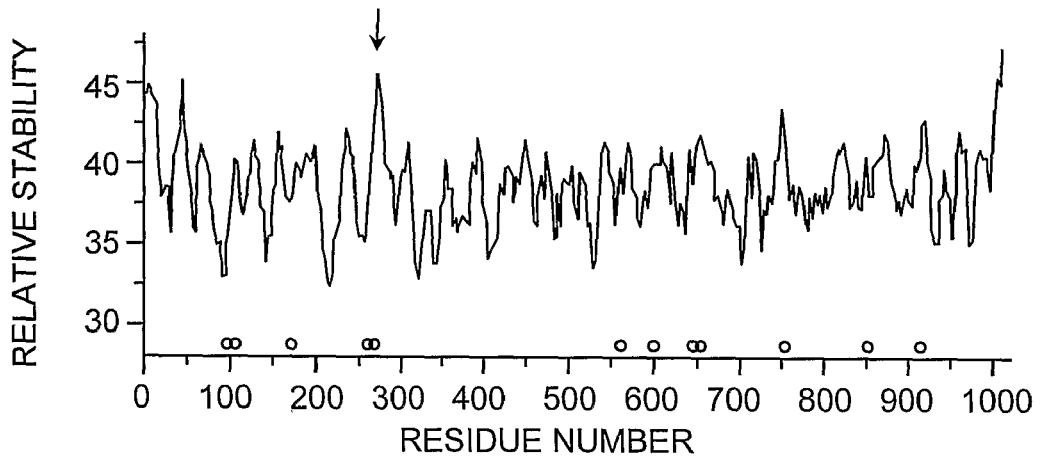
Figure 4C:
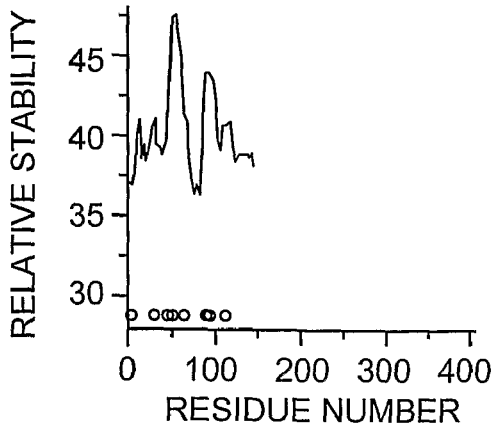
Figure 4D:
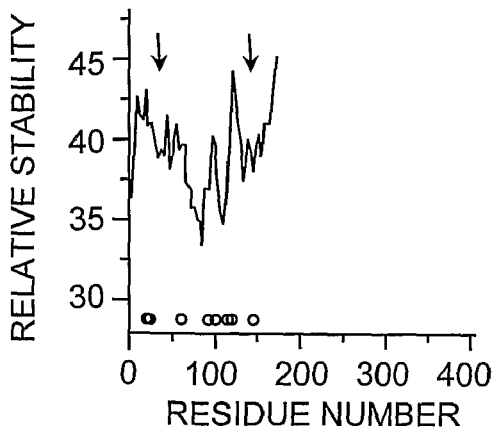

FIG. 3 shows a plot of observed versus predicted $T_m$ values for the peptides listed in Table 3. The solid line shows the best fit, with a correlation of r=0.83.

FIG. 4 shows the calculated relative stability profiles for collagen type I (heterotrimer; FIG. 4A), collagen type II (FIG. 4B), the Scl1 collagen-like protein of *Streptococcus pyogenes* (FIG. 4C), and the collagenous tail of asymmetric acetylcholinesterase (FIG. 4D). The arrows indicate the low stability sites of cross-linking (residues 87 and 930) in type I collagen, the location of the dominant T-cell epitope in type II collagen, and the heparin binding sites in asymmetric acetylcholinesterase. The locations of Lys-Gly-Glu/Asp stabilizing sequences are shown by circles.

Figure 5:
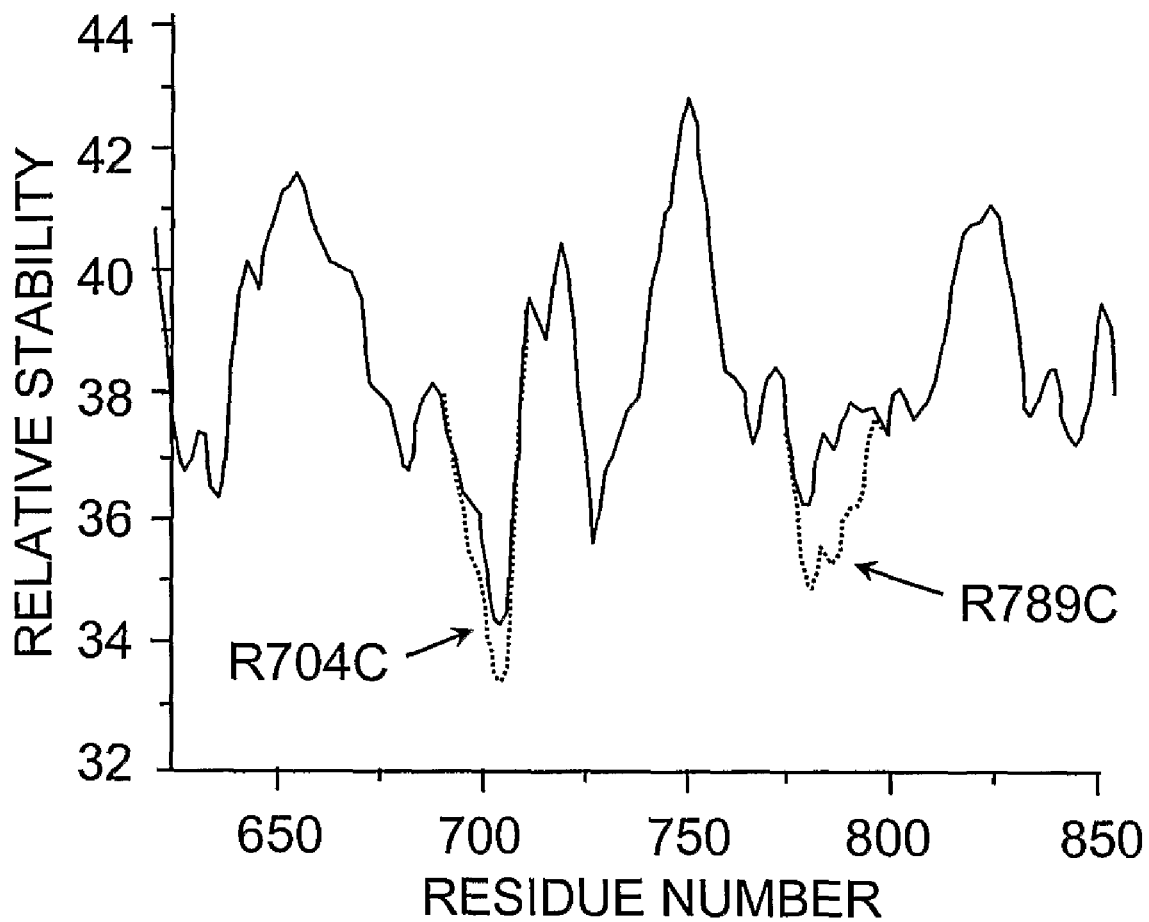

FIG. 5 shows the effect of two mutations resulting in cartilage disorders on the calculated relative stability of type II collagen (residues 625-850 are shown). The altered stability as a result of an Arg to Cys replacement at position 704 (Xaa$_1$ position, leading to a case of achondrogenesis-hypochondrogenesis type II) and at position 789 (Xaa$_2$ position, leading to a case of spondyloepiphyseal dysplasia congenita) are indicated by dotted lines (Ballo, et al. (1998) *Am. J. Med. Genet.* 80:6-11; Chan, et al. (1993) *J. Biol. Chem.* 268:15238-15245).

DETAILED DESCRIPTION OF THE INVENTION

A method for predicting global melting temperatures ($T_m$) of collagen triple helical peptides and short fragments has now been developed. Good agreement was observed between predicted and observed stabilities of a number of collagen peptides and collagen-like peptides. In cases in which the predicted $T_m$ was significantly different from that observed, interactions involving long-range electrostatic interactions or unraveling of the ends were identified. The variations in stability along the collagen chain appeared to be related to known functional sites, and high stability was achieved through a combination of stabilizing imino acids and Lys-Gly-Glu/Asp sequences.

About 80% of mutations in disease have been found to lead to protein destabilization in globular proteins (Wang and Moult (2001) supra), and destabilization appears to correlate well with collagen disease and severity as well (Persikov, et al. (2004) supra; Beck, et al. (2000) *Proc. Natl. Acad. Sci. USA* 97:4273-4278). Predicting the effect of single amino acid replacements in the Xaa$_1$ or Xaa$_2$ positions on collagen stability is now possible, as is the evaluation of the stability of the region in which the mutation occurs. In this regard, the instant method finds application in the design of novel triple helical constructs for production in recombinant systems and applications in biomaterial and tissue engineering structures (Werkmeister, et al. (2003) in *Biomaterials Handbook*. Wise, et al., eds, pp. 229-251, Marcell Dekker, New York).

Experimental data on host-guest triple helical peptides, using a (Gly-Pro-Hyp)$_8$ (SEQ ID NO:1) host, have provided information on the propensities of individual residues for the Xaa$_1$ and Xaa$_2$ positions of Gly-Xaa$_1$-Xaa$_2$ triplets, the interactions within the triple helix for a given Gly-Xaa$_1$-Xaa$_2$ sequence, and the interactions resulting from neighboring tripeptide sequences (Persikov, et al. (2000) *Biochemistry* 39:14960-14967; Persikov, et al. (2002) *J. Mol. Biol.* 316:385-394; Persikov, et al. (2005) *Biochemistry* 44:1414-1422). These data establish the basis for determining the loss of stability that results from replacing Gly-Pro-Hyp tripeptide sequences by other Gly-Xaa$_1$-Xaa$_2$ sequences, thereby defining a set of rules for relating amino acid sequence and stability.

The propensity measurements for all 20 amino acid residues in the Xaa$_1$ position in a Gly-Xaa$_1$-Hyp context and all 20 amino acid residues in the Xaa$_2$ position in a Gly-Pro-Xaa$_2$ context were determined by measuring thermal stability of host-guest peptides (Persikov, et al. (2000) supra). The most stable tripeptide unit is Gly-Pro-Hyp ($T_m$=47.3° C.). Replacing Pro in the Xaa$_1$ position leads to a decrease in stability ranging from 4° C. for Gly-Glu-Hyp ($T_m$=42.9° C.) to 15° C. for Gly-Trp-Hyp ($T_m$=31.9° C.). Replacing Hyp in the Xaa$_2$ position leads to a decrease in stability ranging from almost 0° C. for Gly-Pro-Arg ($T_m$=47.2° C.) to 21° C. for Gly-Pro-Hyp ($T_m$=26.1° C.).

Figure 1:
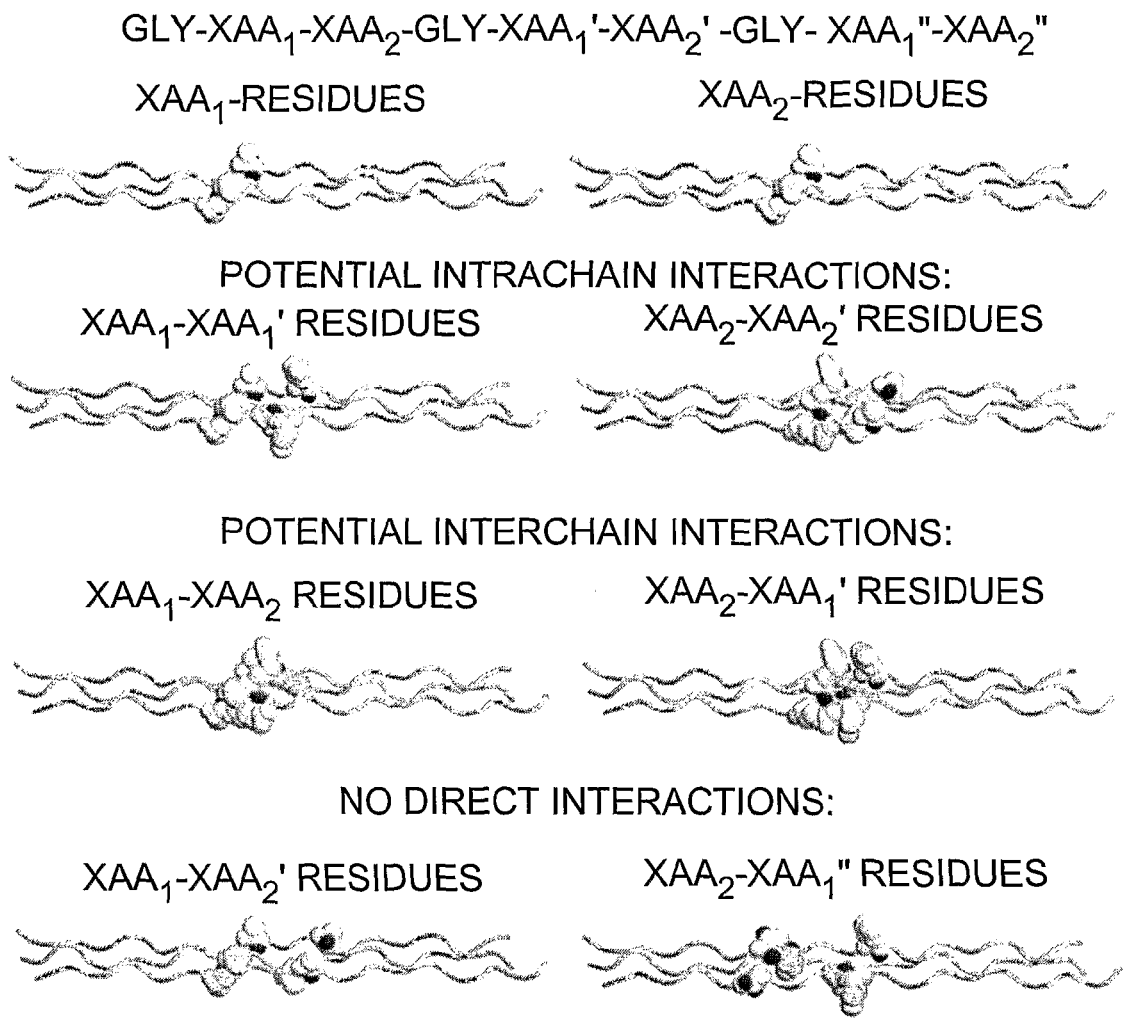
FIG. 1 is a schematic illustration showing the location of $Xaa_1$ and $Xaa_2$ residues within the triple helix and the possibility of intrachain and interchain interactions between residues in adjacent tripeptide units. The bottom panel shows that amino acids separated by >3 residues in sequence are unable to interact directly.

Direct intrachain interactions are not sterically possible between adjacent Xaa$_1$ and Xaa$_2$ residues in the Gly-Xaa$_1$-Xaa$_2$ unit of a chain, but interchain interactions can take place between the Xaa$_2$ residue in one chain and the Xaa$_1$ residue in an adjacent chain staggered by one residue (FIG. 1). Peptides with Gly-Xaa$_1$-Xaa$_2$ guest triplets were designed to model these interchain interactions. Only a restricted set of possible Gly-Xaa$_1$-Xaa$_2$ tripeptides are significantly populated in collagens (Ramshaw, et al. (1998) *J. Struct. Biol.* 122:86-91), reflecting in part strong preferences for basic residues to be in the Xaa$_2$ position and for Glu and hydrophobic residues to be in the Xaa$_1$ position and very low occurrence of Cys, Trp, and Tyr. A limited set of 41 guest Gly-Xaa$_1$-Xaa$_2$ sequences was selected to include the most common tripeptide sequences and to model a range of typical electrostatic and hydrophobic interactions. Because of the strong bias in collagen compositions, the selected 41 Gly-Xaa$_1$-Xaa$_2$, 19 Gly-Xaa$_1$-Hyp, 19 Gly-Pro-Xaa$_2$, and Gly-Pro-Hyp tripeptides cover about 80% of human fibrillar collagen sequences (Persikov, et al. (2002) supra). Although Pro residues in the Xaa$_2$ position are post-translationally modified to Hyp in multicellular animals, collagenous domains have recently been found in bacteria and viruses where there is no hydroxylation of Pro (Rasmussen, et al. (2003) *J. Biol. Chem.* 278:32313-32316; Xu, et al. (2002) *J. Biol. Chem.* 277:27312-27318). To model these sequences, Gly-Pro-Pro and Gly-Ala-Pro guest triplets were also included.

A complete table of the stability for all Gly-Xaa$_1$-Xaa$_2$ triplets was constructed using the experimental values for all frequent sequences and the predicted values for all others (Table 1; experimental values are in bold). Predicted values were calculated on the basis of additivity of residues in the Xaa$_1$ and Xaa$_2$ position (Persikov, et al. (2002) supra; Equation 1).

$$T_m^{GX_1X_2} = T_m^{GX_1O} + T_m^{GPX_2} - T_m^{GPO} \qquad (1)$$

The amino acids in rows in Table 1 are listed in order of their Xaa$_1$ position propensity for triple helix formation, whereas the amino acids in columns are listed in order of their Xaa$_2$ position propensity. Both Pro and Hyp are included in the Xaa$_2$ position.

TABLE 1

| Xaa₁ | Xaa₂ | | | | | | | | | |
|---|---|---|---|---|---|---|---|---|---|---|
| | Hyp | Pro | Arg | Met | Ile | Gln | Ala | Val | Glu | Thr |
| Pro | 47.3 | 45.5 | 47.2 | 42.6 | 41.5 | 41.3 | 40.9 | 40.0 | 39.7 | 39.7 |
| Glu | 42.9 | 41.1 | 40.4 | 38.2 | 37.1 | 37.7 | 34.6 | 35.3 | 35.3 | 35.9 |
| Ala | 41.7 | 37.7 | 38.2 | 37.0 | 35.9 | 35.7 | 32.9 | 34.4 | 34.1 | 34.1 |
| Lys | 41.5 | 39.7 | 39.1 | 36.8 | 35.7 | 38.9 | 35.1 | 34.2 | 35.3 | 33.9 |
| Arg | 40.6 | 38.8 | 38.0 | 35.9 | 34.8 | 34.6 | 34.2 | 33.3 | 33.8 | 33.0 |
| Gln | 40.4 | 38.6 | 39.5 | 35.7 | 34.6 | 34.4 | 34.0 | 33.1 | 32.8 | 32.8 |
| Asp | 40.1 | 38.3 | 37.1 | 35.4 | 34.3 | 34.1 | 31.6 | 32.8 | 32.5 | 32.5 |
| Leu | 39.0 | 37.2 | 36.4 | 34.3 | 33.2 | 35.7 | 31.2 | 31.7 | 31.4 | 31.4 |
| Val | 38.9 | 37.1 | 36.3 | 34.2 | 33.1 | 32.9 | 32.5 | 31.6 | 31.3 | 31.3 |
| Met | 38.6 | 36.8 | 36.0 | 33.9 | 32.8 | 32.6 | 32.2 | 31.3 | 31.0 | 31.0 |
| Ile | 38.4 | 36.6 | 35.8 | 33.7 | 32.6 | 32.4 | 33.9 | 31.1 | 30.8 | 30.8 |
| Asn | 38.3 | 36.5 | 35.7 | 33.6 | 32.5 | 32.3 | 31.9 | 31.0 | 30.7 | 30.7 |
| Ser | 38.0 | 36.2 | 35.4 | 33.3 | 32.2 | 32.0 | 31.6 | 30.7 | 30.4 | 30.4 |
| His | 36.5 | 34.7 | 33.9 | 31.8 | 30.7 | 30.5 | 30.1 | 29.2 | 28.9 | 28.9 |
| Thr | 36.2 | 34.4 | 33.6 | 31.5 | 30.4 | 30.2 | 29.8 | 28.9 | 28.6 | 28.6 |
| Cys | 36.1 | 34.3 | 33.5 | 31.4 | 30.3 | 30.1 | 29.7 | 28.8 | 28.5 | 28.5 |
| Tyr | 34.3 | 32.5 | 31.7 | 29.6 | 28.5 | 28.3 | 27.9 | 27.0 | 26.7 | 26.7 |
| Phe | 33.5 | 31.7 | 30.9 | 28.8 | 27.7 | 27.5 | 24.1 | 26.2 | 25.9 | 25.9 |
| Gly | 33.2 | 31.4 | 30.6 | 28.5 | 27.4 | 27.2 | 26.0 | 25.9 | 25.6 | 25.6 |
| Trp | 31.9 | 30.1 | 29.3 | 27.2 | 26.1 | 25.9 | 25.5 | 24.6 | 24.3 | 24.3 |

| Xaa₁ | Xaa₂ | | | | | | | | | |
|---|---|---|---|---|---|---|---|---|---|---|
| | Cys | Lys | His | Ser | Asp | Gly | Leu | Asn | Tyr | Phe | Trp |
| Pro | 37.7 | 36.8 | 35.7 | 35.0 | 34.0 | 32.9 | 32.7 | 31.7 | 30.2 | 28.4 | 26.1 |
| Glu | 33.3 | 35.0 | 31.3 | 30.6 | 29.7 | 28.5 | 28.3 | 29.5 | 25.8 | 24.0 | 21.7 |
| Ala | 32.1 | 30.8 | 30.1 | 33.0 | 33.0 | 27.3 | 27.8 | 26.1 | 24.6 | 21.9 | 20.5 |
| Lys | 31.9 | 31.0 | 29.9 | 29.2 | 35.8 | 27.1 | 26.9 | 31.7 | 24.4 | 22.6 | 20.3 |
| Arg | 31.0 | 29.5 | 29.0 | 30.5 | 34.5 | 26.2 | 26.0 | 25.0 | 23.5 | 21.7 | 19.4 |
| Gln | 30.8 | 32.6 | 28.8 | 28.1 | 27.1 | 26.0 | 25.8 | 24.8 | 23.3 | 21.5 | 19.2 |
| Asp | 30.5 | 30.9 | 28.5 | 27.8 | 26.8 | 25.7 | 25.5 | 24.5 | 23.0 | 21.2 | 18.9 |
| Leu | 29.4 | 31.1 | 27.4 | 26.7 | 25.7 | 24.6 | 26.9 | 23.4 | 21.9 | 20.1 | 17.8 |
| Val | 29.3 | 32.5 | 27.3 | 26.6 | 25.6 | 24.5 | 24.3 | 23.3 | 21.8 | 20.0 | 17.7 |
| Met | 29.0 | 31.7 | 27.0 | 26.3 | 25.3 | 24.2 | 24.0 | 23.0 | 21.5 | 19.7 | 17.4 |
| Ile | 28.8 | 27.9 | 26.8 | 26.1 | 25.1 | 24.0 | 23.8 | 22.8 | 21.3 | 19.5 | 17.2 |
| Asn | 28.7 | 27.8 | 26.7 | 26.0 | 25.0 | 23.9 | 23.7 | 22.7 | 21.2 | 19.4 | 17.1 |
| Ser | 28.4 | 27.5 | 26.4 | 25.7 | 24.7 | 23.6 | 23.4 | 22.4 | 20.9 | 19.1 | 16.8 |
| His | 26.9 | 26.0 | 24.9 | 24.2 | 23.2 | 22.1 | 21.9 | 20.9 | 19.4 | 17.6 | 15.3 |
| Thr | 26.6 | 25.7 | 24.6 | 23.9 | 22.9 | 21.8 | 21.6 | 20.6 | 19.1 | 17.3 | 15.0 |
| Cys | 26.5 | 25.6 | 24.5 | 23.8 | 22.8 | 21.7 | 21.5 | 20.5 | 19.0 | 17.2 | 14.9 |
| Tyr | 24.7 | 23.8 | 22.7 | 22.0 | 21.0 | 19.9 | 19.7 | 18.7 | 17.2 | 15.4 | 13.1 |
| Phe | 23.9 | 23.0 | 21.9 | 21.2 | 20.2 | 19.1 | 18.9 | 17.9 | 16.4 | 14.6 | 12.3 |
| Gly | 23.6 | 26.9 | 21.6 | 20.9 | 19.9 | 18.8 | 25.3 | 17.6 | 16.1 | 19.7 | 12.0 |
| Trp | 22.3 | 21.4 | 20.3 | 19.6 | 18.6 | 17.5 | 17.3 | 16.3 | 14.8 | 13.0 | 10.7 |

Predicted and experimentally observed (bold) $T_m$ values (in °C.) for all possible Gly-Xaa₁-Xaa₂ tripeptide units in a triple helix, based on host-guest peptide studies.

The predicted values gave good agreement (within ±3° C.) for the Gly-Ala-Ala and for 28 other guest triplets of the 41 Gly-Xaa₁-Xaa₂ triplets studied in host-guest collagen-like peptides. The largest deviations were observed for Gly-Lys-Asp and Gly-Arg-Asp, which were more stable than predicted by 7° C., indicating some interchain electrostatic stabilization. Observed $T_m$ values of Gly-Xaa₁-Arg sequences (Gly-Glu-Arg, Gly-Ala-Arg, Gly-Lys-Arg, Gly-Gln-Arg, and Gly-Asp-Arg) were 2.5° C. smaller on average than predicted, indicating the need for a correction factor in a Gly-Xaa₁-Arg context versus a Gly-Pro-Arg context.

Interactions between adjacent Gly-Xaa₁-Xaa₂ tripeptides were included in the calculations. One study reported stabilities of a selection of host-guest peptides including residues in two adjacent tripeptide units, Gly-Xaa₁-Xaa₂-Gly-Xaa₁'-Xaa₂', covering possible direct interchain or intrachain interactions between residues that are separated by ≦3 residues in sequence (Persikov, et al. (2005) supra) (FIG. 1). Significant deviations from predicted stability were seen for six hexapeptides, which suggested favorable interchain and intrachain electrostatic and hydrophobic interactions (Table 2). The most dramatic difference was the electrostatic and hydrogen bonding stabilization observed when Lys was in the Xaa₂ position and a negatively charged residue was in the Xaa₁ position (Lys-Gly-Asp or Lys-Gly-Glu), with observed $T_m$ values 15.4° C. to 17.5° C. more stable than expected. The large magnitude of Lys-Gly-Asp/Glu interactions was comparable with the $T_m$ spread of all Xaa₁ (14° C.) and Xaa₂ residues (21° C.) (Persikov, et al. (2005) supra) (Table 2).

TABLE 2

| Sequence motif | SEQ ID NO: | $T_m^{pred}$ (° C.) | $T_m^{obs}$ (° C.) | $\Delta T_m$ (° C.) |
|---|---|---|---|---|
| Gly-Xaa-Leu-Gly-Leu-Xaa | 2 | 24.4 | 28.2 | +3.8 |
| Gly-Leu-Xaa-Gly-Leu-Xaa | 3 | 30.7 | 38.1 | +7.4 |
| Gly-Xaa-Lys-Gly-Asp-Xaa | 4 | 29.6 | 47.1 | +17.5 |
| Gly-Xaa-Lys-Gly-Glu-Xaa | 5 | 32.4 | 47.8 | +15.4 |
| Gly-Glu-Xaa-Gly-Xaa-Lys | 6 | 32.4 | 38.0 | +5.6 |
| Gly-Xaa-Lys-Gly-Xaa-Glu | 7 | 29.2 | 36.5 | +7.3 |

$T_m^{pred}$, predicted $T_m$ values, $T_m^{obs}$, observed $T_m$ values.
Xaa represents any amino acid residue.

Figure 2:
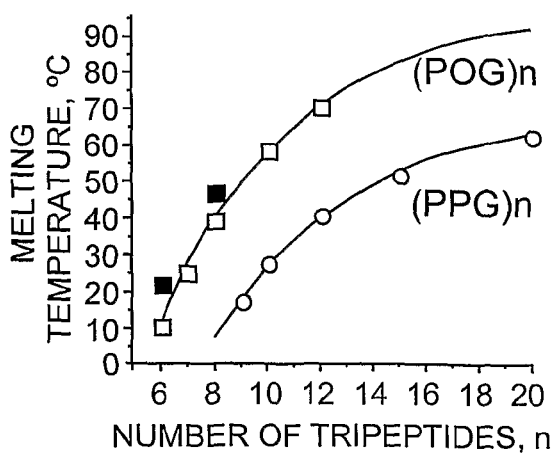
FIG. 2 shows the effect of peptide length on the melting temperatures of unblocked $(Pro-Hyp-Gly)_n$ (open square)

The methodology for determining the global stability of a peptide disclosed herein employs subtraction of the relative stability of the tripeptide sequences that make up a peptide from that expected for the repeating Gly-Pro-Hyp sequence of the same length. The $T_m$ value is seen to depend on n (the number of tripeptide units) for repeating (Gly-Pro-Hyp)$_n$ and (Gly-Pro-Pro)$_n$ peptides (Sutoh and Noda (1974) *Biopolymers* 13:2391-2404; Persikov, et al. (2003) *J. Am. Chem. Soc.* 125:11500-11501). The sharp dependence of stability on length leveling off with increasing n can be fit to a single exponential decay (FIG. 2).

The effect of blocking groups on peptide stability was also taken into consideration. Studies at different pH values and on peptides with and without blocked termini are consistent with a reduction of stability by about 2° C. when unblocked, charged N termini are present and by about 3° C. when unblocked, charged C termini are present, for a peptide length of n=10 (Venugopal, et al. (1994) *Biochemistry* 33:7948-7956). This destabilization is presumed to be due to repulsion when three charged termini are in close proximity, consistent with the unraveling of the termini observed in high resolution structures of collagen peptides (Bella, et al. (1994) supra; Li, et al. (1993) *Biochemistry* 32:7377-7387). End effects are more pronounced for short peptides than for longer ones, as seen for (Pro-Hyp-Gly)$_7$ (SEQ ID NO 8) and for (Pro-Hyp-Gly)$_8$ (SEQ ID NO:9; FIG. 2).

The relative stability of each Gly-Xaa$_1$-Xaa$_2$ tripeptide compared with Gly-Pro-Hyp and the interaction between adjacent Gly-Xaa$_1$-Xaa$_2$ tripeptides were used to derive a method for predicting triple helix stability. The $T_m$ values, rather than Gibbs free energy values, were used for calculating peptide stability. The extremely long times needed to reach equilibrium and the lack of agreement of the equilibrium curve with a two-state model presented practical and theoretical limitations to thermodynamic characterization (Persikov, et al. (2004) supra). Fortunately, the use of $T_m$ values obtained under standardized conditions has proved to be useful as an empirical measure of triple helix stability (Persikov, et al. (2004) supra). Additivity of $T_m$ values was observed for peptides with residues that cannot interact. Thus, $T_m$ values are deemed a good measure of relative stability, as long as standard conditions of buffer, pH, and rate of heating are maintained (Persikov, et al. (2004) supra). The method predicts a global $T_m$ value for collagen model peptides of at least 6 tripeptides in length and predicts a relative stability for collagen sequences.

The global thermal stability of homotrimeric triple helical peptides with length of at least 6 tripeptide units and, in most cases, containing 10 tripeptide units was determined as follows.

For the total number of triplets n in a given peptide, the base $T_m^0(n)$ for (Pro-Hyp-Gly) or (Pro-Pro-Gly)$_n$ was calculated from the length dependence (Equation 1), including any effect of blocking groups;

The melting temperature value was decreased for every triplet in the sequence that was not Gly-Pro-Hyp, subtracting a value of $\Delta T_m^{GXY}$ (Table 1). The N-terminal and C-terminal tripeptide units were excluded from the calculation due to the staggering of the chains and the disorder for the peptide ends (Bella et al. (1994) supra; Li, et al. (1993) *Biochemistry* 32:7377-7387; Kramer, et al. (2001) *J. Mol. Biol.* 301:1191-1205).

The resulting value for the peptide melting temperature was adjusted using the $\Delta T_m^{int}$ values for interactions between neighboring tripeptides (Table 2).

The method was formulated as follows.

$$T_m = T_m^0 - \sum_{i=2}^{n-1} \Delta T_m^{GX_1X_2} + \sum T_m^{int} \quad (3)$$

To demonstrate that the method was suitable for use in calculating global stability of collagen peptides and collagen-like peptides, the stability of 40 synthetic collagen-like peptides and one cyanogens bromide peptide from type I collagen (Table 3) was determined. The $T_m$ values for these peptides were experimentally determined under the same defined standard conditions (Table 4). Most of the peptides were n=10 tripeptide units in length, and some had unblocked ends, whereas others have terminal blocking groups. Excellent agreement was found between the calculated and observed $T_m$ values for peptides with Gly-Pro-Hyp tripeptide units on both ends. For instance, for the unblocked peptide T3-785, the predicted $T_m$ value was 17.1° C. (58.8° C.−[(47.3° C.−30.8° C.)+(47.3° C.−38.2° C.)+(47.3° C.−31.2° C.)]), in close agreement with the observed $T_m$ of 18.0° C. When Lys-Gly-Glu or Lys-Gly-Asp sequences were present, agreement was dependent on the inclusion of $\Delta T_m^{int}$ correction values for interactions between adjacent triplets. For instance, peptide T1-655, which has Gly-Pro-Hyp caps on both ends, has an observed $T_m$ value of 42.8° C. If each independent triplet was considered, one would subtract 16.5° C. for Gly-Ala-Lys, 15.7° C. for Gly-Asp-Ala, and 6.4° C. for Gly-Pro-Ala, yielding 58.8° C.−38.6° C.=20.2° C. However, there was a Lys-Gly-Asp sequence, which gave +17.5° C., and an increase of 5° C. because the ends were blocked, giving a net predicted value of 42.7° C., which was very close to the observed value of 42.8° C. The set of peptides related to T1-892 with Gly-Pro-Ala sequences on the N-terminal ends also showed excellent agreement with predictions. It was notable that the "reverse" peptide, T1-892r, which had the same tripeptide composition but in a different order, had the same $T_m$ as T1-892, supporting the dependence of thermal stability on tripeptide unit composition when there were no interactions present (Tables 3 and 4) (Buevich, et al. (2004) *J. Biol. Chem.* 279:46890-46895).

TABLE 3

| Name | Sequence | SEQ ID NO: |
|---|---|---|
| T1-655 | Ac-(GPO)$_3$-GAK-GDA-GPO-GPA-(GPO)$_3$-GY-NH$_2$ | 10 |
| T1-892[a] | Ac-GPA-GPA-GPV-GPA-GAR-GPA-(GPO)$_4$-GV-NH$_2$ | 11 |
| T1-892r[b] | Ac-(GPO)$_4$-GPA-GPA-GPV-GPA-GAR-GPA-GV-NH$_2$ | 12 |
| T1-892 (P26A)[c] | Ac-(GPA)$_2$-GPV-GPA-GAR-GPA-(GPO)$_2$-GAO-GPO-GV-NH$_2$ | 13 |
| T1-892 (O24A)[c] | Ac-(GPA)$_2$-GPV-GPA-GAR-GPA-GPO-GPA-(GPO)$_2$-GV-NH$_2$ | 14 |
| T1-892 unbl | GPA-GPA-GPV-GPA-GAR-GPA-(GPO)$_4$-GY | 15 |
| T1-904[a] | Ac-GAR-GPA-GPQ-GPR-GDK-GET-(GPO)$_4$-GV-NH$_2$ | 16 |
| T1A2-697 | Ac-GFO-GAA-GRT-GPO-GPS-GIS-(GPO)$_4$-GV-NH$_2$ | 17 |

TABLE 3-continued

| Name | Sequence | SEQ ID NO: |
|---|---|---|
| T2-508 | Ac-GSO-GAQ-GLQ-GPR-GLO-GTO-(GPO)$_4$-GV-OH | 18 |
| T3-505[d] | Ac-GGK-GDA-GAO-GER-GPO-GLA-(GPO)$_4$-GV | 19 |
| T3-508[d] | Ac-GDA-GAO-GER-GPO-GLA-GAO-(GPO)$_4$-GV | 20 |
| T3-511[d] | Ac-GAO-GER-GPO-GLA-GAO-GLR-(GPO)$_4$-GV | 21 |
| T3-514[d] | Ac-GER-GPO-GLA-GAO-GLR-GGA-(GPO)$_4$-GV | 22 |
| T3-517[d] | Ac-GPO-GLA-GAO-GLR-GGA-GPO-(GPO)$_4$-GV | 23 |
| T3-520[d] | Ac-GLA-GAO-GLR-GGA-GPO-GPE-(GPO)$_4$-GV | 24 |
| T3-772[d] | Ac-GPO-GAO-GPL-GIA-GIT-GAR-GLA-(GPO)$_4$-GG-NH$_2$ | 25 |
| T3-785[d] | PO-(GPO)$_2$-GIT-GAR-GLA-(GPO)$_4$-G | 26 |
| T3-997[d] | Ac-GPR-GNR-GER-GSE-GSO-GHO-GQO-GPO-GPO-GAO-GV-NH$_2$ | 27 |
| T7-2031 | Ac-GLA-GEO-GKO-GIO-GLO-GRA-(GPO)$_4$-GV-NH$_2$ | 28 |
| T7-2058 | Ac-GER-GER-GEK-GER-GEQ-GRD-(GPO)$_4$-GV-NH$_2$ | 29 |
| AchE-HG-C1[e] | Ac-GPO-GPO-GPO-GKR-GKO-GPO-GPO-GPO-GG-NH$_2$ | 30 |
| AchE-HG-C2[e] | Ac-GPO-GPO-GRO-GKR-GKO-GPO-GPO-GPO-GG-NH$_2$ | 31 |
| AchE-HG-C3[e] | Ac-GPO-GPO-GRO-GKR-GKQ-GPO-GPO-GPO-GG-NH$_2$ | 32 |
| AchE-HG-Alt[e] | Ac-GPO-GPO-GRQ-GKR-GKO-GPO-GPO-GPO-GG-NH$_2$ | 33 |
| AchE-HG-C4[e] | Ac-GPO-GPO-GRO-GKR-GKQ-GQK-GPO-GPO-GG-NH$_2$ | 34 |
| AchE-HG-N1[e] | Ac-GPO-GPO-GPO-GRK-GRO-GPO-GPO-GPO-GG-NH$_2$ | 35 |
| AchE-HG-N2[e] | Ac-GPO-GPO-GRO-GRK-GRO-GPO-GPO-GPO-GG-NH$_2$ | 36 |
| AchE-146 (t)[f] | PO-GRO-GRK-GRO-GVR-GPR-(GPO)$_4$-G-NH$_2$ | 37 |
| AchE-146A(t)[f] | PO-GRO-GAA-GAO-GVR-GPR-(GPO)$_4$-G-NH$_2$ | 38 |
| AchE-146B(t)[f] | PO-GAO-GRK-GRO-GVA-GPA-(GPO)$_4$-G-NH$_2$ | 39 |
| AchE-251 (t)[f] | PO-GRO-GKR-GKT-GLK-GDI-(GPO)$_4$-G-NH$_2$ | 40 |
| AchE-224 (t)[f] | PO-GLO-GML-GQK-GEM-GPK-(GPO)$_4$-G-NH$_2$ | 41 |
| AchE-146/241[g] | PO-GRO-GKR-GKO-GVR-GPR-(GPO)$_4$-G-NH$_2$ | 42 |
| AchE-P126 (r)[f] | Ac-GPO-GPO-GRO-GRK-GRO-(GPO)$_5$-G-NH$_2$ | 43 |
| AchE-P231 (r)[f] | Ac-GPO-GPO-GRO-GKR-GKQ-GQK-(GPO)$_4$-G-NH$_2$ | 44 |
| MSR-1[h] | PO-(GPO)2-GPK-GQK-GEK-(GPO)$_4$-G | 45 |
| MBL 42-61[i] | Ac-GIN-GFO-GKD-GRD-GTK-GEK-GEO-(GPO)$_4$-GG-NH$_2$ | 46 |
| MBL 45-61[i] | GFO-GKD-GRD-GTK-GEK-GEO-(GPO)$_4$-GY | 47 |
| C1qA-15 | Ac-GPO-GRO-GRR-GRO-GLK-GEQ-(GPO)$_4$-GY-NH$_2$ | 48 |
| C1qC-67 | Ac-GPO-GIR-GPK-GQK-GEO-GLO-(GPO)$_4$-GY-NH$_2$ | 49 |
| α1CB2[j] | GPS-GPR-GLO-GPO-GAO-GPQ-GFQ-GPO-(GEO)$_2$-GAS-GPM | 50 |

[a] Yang et al. (1997) Biochemistry 36:6930-6935.
[b] Buevich, et al. (2004) supra.
[c] Xu, et al. (2003) Biochemistry 42:8696-8703.
[d] Shah, et al. (1997) Biochemistry 36:5878-5883.
[e] Doss-Pepe, et al. (2004) Biochim. Biophys. Acta 1698:187-195.
[f] Deprez, et al. (2000) Biochem. J. 350:283-290.
[g] Doss-Pepe, et al. (2000) Biochemistry 39:14884-14892.
[h] Anachi, et al. (1995) FEBS Lett. 368:551-555.
[i] Mohs, et al. (2005) Biochemistry 44:1793-1799.
[j] Piez and Sherman (1970) Biochemistry 9:4134-4140.

TABLE 4

| Name | $T_m^{pred}$ | $T_m^{obs}$ | $\Delta T_m$ |
|---|---|---|---|
| T1-655 | 42.7 | 42.8 | 0.1 |
| T1-892 | 28.2 | 26.0 | −2.2 |
| T1-892r | 28.2 | 26.0 | −2.2 |
| T1-892 (P26A) | 22.6 | 24.1 | 1.5 |
| T1-892 (O24A) | 21.8 | 23.2 | 1.4 |
| T1-892 unbl | 23.2 | 20.6 | −3.2 |
| T1-904 | 38.9 | 30.8 | −8.1 |
| T1A2-697 | 1.6 | <4 | + |
| T2-508 | 21.1 | 25.0 | 3.9 |
| T3-505 | 25.3 | 20.9 | −4.4 |
| T3-508 | 26.6 | 23.2 | −3.4 |
| T3-511 | 21.3 | 25.9 | 4.6 |
| T3-514 | 6.9 | 16.5 | 9.6 |
| T3-517 | 6.9 | 15.8 | 8.9 |
| T3-520 | 15.4 | 17.5 | 2.1 |
| T3-772 | −4.5 | <4 | + |
| T3-785 | 17.1 | 18.0 | 0.9 |
| T3-997 | 1.4 | <4 | + |
| T7-2031 | 23.3 | 25.4 | 2.1 |
| T7-2058 | 36.3 | 23.2 | −13.1 |
| AchE-HG-C1 | 33.3 | 32.3 | −1.0 |
| AchE-HG-C2 | 26.6 | 26.9 | 0.3 |
| AchE-HG-C3 | 24.0 | 21.3 | −2.7 |
| AchE-HG-Alt | 20.6 | 20.1 | −0.5 |
| AchE-HG-C4 | 9.3 | 8.1 | −1.2 |
| AchE-HG-N1 | 22.8 | 22.2 | −0.6 |
| AchE-HG-N2 | 16.1 | 17.4 | 1.3 |
| AchE-146 (t) | 18.5 | 15.5 | −3.0 |
| AchE-146A (t) | 23.0 | 18.6 | −4.4 |
| AchE-146B (t) | 9.5 | 11.0 | 1.5 |
| AchE-251 (t) | 20.9 | 9.8 | −11.1 |
| AchE-224 (t) | 15.9 | 7.0 | −8.9 |
| AchE-146/241 | 29.0 | 19.7 | −9.3 |
| AchE-P126 (r) | 32.6 | 30.0 | −2.6 |
| AchE-P231 (r) | 25.8 | 23.9 | −1.9 |
| MSR-1 | 36.7 | 30.0 | −6.7 |
| MBL 42-61 | 25.2 | 23.0 | −2.2 |
| MBL 45-61 | 27.0 | 17.9 | −9.1 |
| C1qA-15 | 30.7 | 23.3 | −7.4 |
| C1qC-67 | 29.8 | 28.4 | −1.4 |
| α1CB2 | 8.6 | 12 | 3.4 |

$T_m^{pred}$, predicted $T_m$ values, $T_m^{obs}$, observed $T_m$ values.

Applying the method to the peptides of Table 3, the predicted $T_m^{pred}$ values showed excellent agreement (within +2° C.) for 14 peptides and an overall correlation coefficient of r=0.83 (Table 4; FIG. 3). However, in a number of cases, the predicted values differed from experimental $T_m$ values by >4° C. Predicted values were consistently higher than observed ones for peptides containing consecutive strings of positively and negatively charged residues: T7-2058 (Gly-Glu-Arg-Gly-Glu-Lys-Gly-Glu-Arg-Gly-Glu-Gln; SEQ ID NO:51), T1-904 (Gly-Pro-Arg-Gly-Asp-Lys-Gly-Glu-Thr; SEQ ID NO:52), MBL (Gly-Lys-Asp-Gly-Arg-Asp-Gly-Thr-Lys-Gly-Glu-Lys-Gly-Glu-Hyp; SEQ ID NO; 53), and MSR-1 ( Gly-Pro-Lys-Gly-Gln-Lys-Gly-Glu-Lys; SEQ ID NO:54). This indicated that there were long-range effects in strings of residues of opposite charge such that additivity of individual triplets plus Lys-Gly-Glu/Asp effects may not apply. Examination of peptides including highly basic sequences from the heparin binding region of the collagenous tail of the asymmetric form of acetylcholinesterase points to a potential destabilizing effect of charge repulsion at the uncapped N terminus. When these highly basic sequences were included in a host-guest context, with Gly-Pro-Hyp caps at both ends, there was very good agreement between predicted and observed $T_m$ values. However, when there was an uncapped N terminus, the experimental $T_m$ values were often lower than those predicted. Not wishing to be bound by theory, it is believed that charge repulsion leads to unraveling at the N terminus and a lower than expected stability.

To demonstrate that the method was suitable for use in calculating local stability variations in collagens and collagen-like domains of full-length collagen proteins, the thermal stability prediction method was applied to collagen-like domains and full-length collagens. For this purpose, the thermal stability prediction method was modified because of length and the presence of multiple cooperative units during unfolding. Following the averaging approach set forth in the art (Bachinger and Davis (1991) Int. J. Biol. Macromol. 13:152-156; Bachinger, et al. (1993) Am. J. Med. Genet. 45:152-162), the instant method was applied to determine thermally stable and labile domains along the triple helix. A stability coefficient was assigned for every Gly-Xaa$_1$-Xaa$_2$ triplet (Table 1) and corrected for the interaction between triplets (Table 2). The stability was averaged over a window of five tripeptide units, with the average relative stability value for the triplet i equal to the average of the stability coefficients in the interval [i−2, i+2], inclusive. The averaged relative stability values were plotted against the tripeptide number in collagen sequence. For heterotrimer sequences, the values of the three individual collagen chain sequences were averaged. Averages over a shorter or longer set of tripeptide units are also contemplated.

To illustrate the application of the method to collagens and collagen-like domains, stability profiles were calculated for the type I collagen heterotrimer and the homotrimers of type II collagen, the collagenous domain (ColQ) of the asymmetric form of acetylcholinesterase and the collagen domain of the bacterial protein Scl1 of S. pyogenes (FIG. 4). The profiles showed that the average stability along most of the molecules stays in an intermediate range on a relative scale (FIG. 4), with a small number of local regions of high and low stability. Examination of type I collagen showed that the C-terminal region had the highest stability, whereas two regions of low stability were identified as the cross-linking sites Lys-Gly-His-Arg (SEQ ID NO:55), at residues 87 and 930. For type II collagen, the highest stability peaks were seen at both ends, together with a very strong peak near residue 271, the site of immunodominant T-cell epitope in type II collagen implicated in rheumatoid arthritis (residues 261-273; Andersson, et al. (1998) Proc. Natl. Acad. Sci. USA 95:7574-7579). The bacterial Scl1 protein (Xu, et al. (2002) J. Biol. Chem. 277: 27312-27318) showed two peaks at regions rich in Lys-Gly-Glu/Asp sequences, and the two heparin binding sites can be located along the stability profile of the ColQ tail of acetylcholinesterase (Deprez, et al. (2000) Biochem. J. 350:283-290).

It has been suggested that regions of high imino acid content are the most stable, whereas regions deficient in imino acids are less stable. Examination of the stability profiles shows that regions lacking imino acids often contain Lys-Gly-Glu/Asp sequences and thus are quite stable. A wide range of Lys-Gly-Glu/Asp contents was observed in different collagens, ranging from 3% in type I and II collagens to 10% in type IV collagen in basement membranes (Table 5). The high Lys-Gly-Glu/Asp content may provide stability to compensate for the numerous destabilizing interruptions present in type IV collagen. The very high Lys-Gly-Glu/Asp content of some bacterial proteins, such as 20% for Scl1 (Xu, et al. (2002) supra), indicates the importance of electrostatic stabilization when the imino acid content is low and Hyp is absent (Table 5).

TABLE 5

| Protein | Imino Acids | | Lys-Gly-Glu + Lys-Gly-Asp | |
|---|---|---|---|---|
| | Total No. | % of $Xaa_1$ + $Xaa_2$ | Total No. | % of Triplets |
| COL1A1 | 236 | 35% | 6 + 6 | 3.6% |
| COL2A1 | 224 | 33% | 9 + 3 | 3.6% |
| COL4A1 | 307 | 33% | 25 + 23 | 10.3% |
| AchE | 38 | 33% | 5 + 3 | 13.8% |
| Scl1 | 15 | 15% | 6 + 4 | 20.4% |

The ability to calculate stability profiles from amino acid sequence allows for the analysis of collagen mutations. It is now possible to determine whether a mutation is occurring in a region of low or high stability and is of clinical significance (Bachinger, et al. (1993) supra). In the case of mutations in the $Xaa_1$ and $Xaa_2$ positions, it is also now possible to recalculate the profile with the amino acid change to see whether mutations lead to significant destabilization, as proposed for deleterious mutations in globular proteins. The sites of two mutations in type II collagen, one leading to achondrogenesis-hypochondrogenesis (Ballo, et al. (1998) *Am. J. Med. Genet.* 80:6-11) and the other to spondyloepiphyseal dysplasia congenital (Chan, et al. (1993) *J. Biol. Chem.* 268:15238-15245), were both shown to lead to local destabilization (FIG. 5).

The instant method uses amino acid sequence to determine $T_m$ values of peptides and to determine stability variations along proteins in a quantitative manner. Determining the relationship between amino acid sequence and stability is possible for the collagen triple helix because of its linear nature, which limits interactions to be local, involving residues close in sequence; the small size of the repeating unit Gly-$Xaa_1$-$Xaa_2$; and the strong preferential occurrence of a limited number of possible sequence combinations. The method derived from peptide studies herein gives good predictions for the $T_m$ values of many collagen-like peptides, indicating that the important propensities and interactions are valid.

In accordance with the teachings herein, the present invention is a method for determining the global or overall thermal stability of a collagen peptide, collagen-like peptide or triple-helix construct, and for determining local stability variations in collagens and collagen-like domains of full-length proteins. As used in the context of the present invention, a collagen peptide, collagen-like peptide or triple-helix construct is a peptide having a primary amino acid sequence with consecutive repeating units of the tripeptide (Gly-$Xaa_1$-$Xaa_2$)$_n$, wherein $Xaa_1$ and $Xaa_2$ are any amino acid residue and n is at least 6. A peptide, as used in the context of the present invention, is generally 10 to 100 amino acids in length, whereas a protein or full-length protein is 100 amino acids in length or more. The global thermal stability of such a peptide, as defined by the melting temperature, can be accurately determined using the instant method. As exemplified herein, the predicted melting temperatures of a plurality of collagen and collagen-like peptides were in agreement (±7° C.) with observed melting temperatures for these peptides under standard conditions of buffer, pH, and rate of heating (Persikov, et al. (2004) supra)

According to the method of the present invention, the first step involves identifying the number of consecutive Gly-$Xaa_1$-$Xaa_2$ amino acid repeats in the collagen peptide, collagen-like peptide or triple-helix construct. This step of the method can be carried out by visual or computer-based inspection of the primary amino acid sequence of the collagen peptide, collagen-like peptide or triple-helix construct. Upon identification of the repeating unit of (Gly-$Xaa_1$-$Xaa_2$)$_n$, wherein n is at least 6, the maximum melting temperature of a collagen peptide, collagen-like peptide or triple-helix construct of this length is determined. As used herein, the maximum melting temperature of a collagen peptide, collagen-like peptide or triple-helix construct is based upon the melting temperature of a peptide containing repeating units of the highly stable Gly-Pro-Hyp triplet. As set forth in FIG. 2, the melting temperature of a (Gly-Pro-Hyp)$_n$ peptide is dependent upon the number n of repeating units. In this regard, the maximum melting temperature of each Gly-$Xaa_1$-$Xaa_2$ repeat is a function of, or relates, to the melting temperature of a (Gly-Pro-Hyp)$_n$ peptide, wherein n corresponds to the number of consecutive Gly-$Xaa_1$-$Xaa_2$ amino acid repeats in the collagen peptide, collagen-like peptide or triple-helix construct.

After determining the maximum melting temperature of the collagen peptide, collagen-like peptide or triple-helix construct, Gly-$Xaa_1$-$Xaa_2$ repeats which do not conform with the stable sequence Gly-Pro-Hyp are identified. The destabilizing effect of a $Xaa_1$ which is not Pro or a $Xaa_2$ which is not Hyp, is taken into account by adjusting or decreasing the melting temperature of each Gly-$Xaa_1$-$Xaa_2$ repeat by a reference temperature corresponding to each Gly-$Xaa_1$-$Xaa_2$. In particular embodiments, the reference temperatures for Gly-$Xaa_1$-$Xaa_2$ repeats are set forth herein in Table 1. In other embodiments, the N-terminal and C-terminal tripeptide repeats are excluded. Because of the additivity of melting temperature values for peptides with residues that cannot interact, the adjusted melting temperatures for all Gly-$Xaa_1$-$Xaa_2$ repeats of the collagen peptide, collagen-like peptide or triple-helix construct are combined thereby providing a correction melting temperature.

The destabilizing effect of all Gly-$Xaa_1$-$Xaa_2$ on the global thermal stability of the collagen peptide, collagen-like peptide or triple-helix construct is accounted for by adjusting or decreasing the maximum melting temperature of the collagen peptide, collagen-like peptide or triple-helix construct with the correction melting temperature. The result is a melting temperature value indicative of the thermal stability of the collagen peptide, collagen-like peptide or triple-helix construct.

In a further embodiment, the instant method is applied to the location of regions or domains of high and low stability within an entire collagen protein or within a collagen-like domain. In accordance with this embodiment, melting temperatures are averaged over a window of two to 10 tripeptide units depending upon the application. In particular embodiments, melting temperatures are averaged over a window of five tripeptide units.

As exemplified herein, particular combinations of neighboring Gly-$Xaa_1$-$Xaa_2$ peptides have a stabilizing effect on collagen peptide, collagen-like peptide or triple-helix construct. These stabilizing sequence motifs are presented in Table 3. To take these stabilizing sequence motifs into consideration, particular embodiments of the instant method embrace the additional steps of identifying the presence of one or more stabilizing sequence motifs in the collagen peptide, collagen-like peptide or triple-helix construct and adjusting the melting temperature of the collagen peptide, collagen-like peptide or triple-helix construct when a stabilizing sequence motif is present. Adjustments are made based on the increase in melting temperature imparted by the stabilizing sequence motifs as set forth in Table 3.

The instant method finds application in recombinant protein technology to determine whether a collagen peptide, collagen-like peptide or triple-helix construct will be stable for its intended purpose, e.g., in tissue engineering or reconstruction, and whether replacement of specific amino acids by other residues will increase or decrease overall stability. Domains of low stability can be engineered to improve stability. Further, collagens, collagen-like peptides or triple-helix constructs can be assessed to determine whether a disease-causing mutation which destabilizes the protein is present and thereby leading to a disease phenotype. Moreover, using the instant method, a collagen peptide, collagen-like peptide or triple-helix construct with a predetermined thermal stability can be designed to have, e.g., a higher or lower stability region as compared to a wild-type version of the collagen peptide, collagen-like peptide or triple-helix construct. Design of such peptides or constructs is carried out by making modifications to existing collagen, collagen-like or triple-helix sequences.

Desirably, the instant method is carried out using a computer system. Accordingly, the present invention also relates to a computer software program which, once executed by a computer processor, performs the instant method. The present invention further relates to a computer program product involving a computer software program which, once executed by a computer processor, performs the method of the present invention.

A computer system, according to the present invention, refers to a computer or a computer-readable medium designed and configured to perform some or all of the method steps as disclosed herein. A computer, as used herein, can be any of a variety of types of general-purpose computers such as a personal computer, network server, workstation, or other computer platform currently in use or which will be developed. As commonly known in the art, a computer typically contains some or all the following components, for example, a processor, an operating system, a computer memory, an input device, and an output device. A computer can further contain other components such as a cache memory, a data backup unit, and many other devices well-known in the art. It will be understood by those skilled in the relevant art that there are many possible configurations of the components of a computer.

A processor, as used herein, can include one or more microprocessor(s), field programmable logic arrays(s), or one or more application-specific integrated circuit(s). Illustrative processors include, but are not limited to, INTEL® Corporation's PENTIUM® series processors, Sun Microsystems' SPARC® processors, Motorola Corporation's POWERPC™ processors, MIPS® processors produced by MIPS® Technologies Inc., Xilinx Inc.'s processors, and other processors that are or will become available.

An operating system, as used herein, encompasses machine code that, once executed by a processor, coordinates and executes functions of other components in a computer and facilitates a processor to execute the functions of various computer programs that can be written in a variety of programming languages. In addition to managing data flow among other components in a computer, an operating system also provides scheduling, input-output control, file and data management, memory management, and communication control and related services, all in accordance with known techniques. Exemplary operating systems include, for example, the readily available WINDOWS® operating system from the MICROSOFT® Corporation, UNIX® or LINUX™ type operating system, MACINTOSH® operating system from APPLE®, and the like or a future operating system, and some combination thereof.

As used herein, a computer memory can be any of a variety of known or future memory storage devices. Examples include, but are not limited to, any commonly available random access memory (RAM), magnetic medium such as a resident hard disk or tape, an optical medium such as a read and write compact disc or digital versatile disc, or other memory storage device. Memory storage devices can be any of a variety of known or future devices, including a compact disk drive, a digital versatile disc drive, a tape drive, a removable hard disk drive, or a diskette drive. Such types of memory storage device typically read from, and/or write to, a computer program storage medium such as, respectively, a compact disk, a digital versatile disc, magnetic tape, removable hard disk, or floppy diskette. Any of these computer program storage media, or others now in use or that may later be developed, can be considered a computer program product. As will be appreciated, these computer program products typically store a computer software program and/or data. Computer software programs typically are stored in a system memory and/or a memory storage device.

An input device, as referred to herein, can include any of a variety of known devices for accepting and processing information from a user, whether a human or a machine, whether local or remote. Such input devices include, for example, modem cards, network interface cards, sound cards, keyboards, or other types of controllers for any of a variety of known input function. An output device can include controllers for any of a variety of known devices for presenting information to a user, whether a human or a machine, whether local or remote. Such output devices include, for example, modem cards, network interface cards, sound cards, display devices (for example, monitors or printers), or other types of controllers for any of a variety of known output function. If a display device provides visual information, this information typically can be logically and/or physically organized as an array of picture elements, sometimes referred to as pixels.

As will be evident to those skilled in the relevant art, a computer software program of the present invention can be executed by being loaded into a system memory and/or a memory storage device through input devices. On the other hand, all or portions of the software program can also reside in a read-only memory or similar device of memory storage device, such devices not requiring that the software program first be loaded through input devices. It will be understood by those skilled in the relevant art that the software program or portions of it can be loaded by a processor in a known manner into a system memory or a cache memory or both, as advantageous for execution.

It is contemplated that not only can the computer program product or the computer software program be stored on and/or executed by a computer or a computer server, network systems composed of hardware and software can also be employed. Examples of network systems may include arrangement over any media including Internet, ETHERNET™ 10/1000, IEEE 802.11x, IEEE 1394, XDSL, BLUETOOTH®, 3G, or any other ANSI-approved standard. When the computer is linked to a microarray instrument through a network system, microarray data are sent out through an output device of the microarray instrument and received through an input device of a computer having the computer program product or software. The computer program product or the software then processes the microarray data and estimates missing values according to methods of the present invention. It is also contemplated that the microarray data can be stored in a server in a network system, the computer software of the present invention is executed in the server or through a separate computer, and resulting information is presented to a user in the presence of an output of a computer.

The invention is described in greater detail by the following non-limiting examples.

EXAMPLE 1

Materials and Methods

The $T_m$ values of all host-guest peptides were measured under a set of standard conditions, with c=1 mg/ml in phosphate-buffered saline, pH 7.0, and with a heating rate average of 0.1° C./minute (Persikov, et al. (2004) supra). Small variations were seen at acid versus neutral pH, but all calculations were based on host-guest peptide data collected at pH 7.

The (Pro-Hyp-Gly)$_n$ peptides for n=6, 7, 8, and 12 were synthesized by Tufts Core Facility (Boston, Mass.) and purified using high pressure liquid chromatography; their identity was confirmed by matrix-assisted laser desorption ionization.

To extrapolate the dependence of the $T_m$ of the host peptides on peptide length, the experimental values for (Pro-Hyp-Gly)$_n$ and (Pro-Pro-Gly)$_n$ versus n, where n is the number of tripeptide units, were fit to the exponential decay function $$T_m^0 = T_m^{max} - A \cdot \exp\left(-\frac{n}{n_0}\right) \tag{3}$$

where $T_m^0(n)$ is defined as the base thermal stability of the repeating polytripeptide standard, $T_m^{max}$ is the maximum melting temperature, and the constant $n_0$ represents the length of the repeating peptide with $T_m=0$.

---

What is claimed is:

1. A method for determining the thermal stability of a collagen peptide, collagen-like peptide or triple-helix construct comprising
  a) obtaining the primary amino acid sequence of a collagen peptide, collagen-like peptide or triple-helix construct having consecutive repeating units of the tripeptide (Gly-$Xaa_1$-$Xaa_2$)$_n$, wherein $Xaa_1$ and $Xaa_2$ are any amino acid residue and n is at least 6;
  b) identifying the number of consecutive Gly-$Xaa_1$-$Xaa_2$ amino acid repeats in the collagen peptide, collagen-like peptide or triple-helix construct by computer inspection of the primary amino acid sequence of the collagen peptide, collagen-like peptide or triple-helix construct;
  c) determining the maximum melting temperature of the collagen peptide, collagen-like peptide or triple-helix construct relative to the melting temperature of a (Gly-Pro-Hyp)$_n$ peptide, wherein n corresponds to the number of consecutive Gly-$Xaa_1$-$Xaa_2$ amino acid repeats in the collagen peptide, collagen-like peptide or triple-helix construct;
  d) identifying Gly-$Xaa_1$-$Xaa_2$ amino acid repeats in the collagen peptide, collagen-like peptide or triple-helix construct wherein $Xaa_1$ is not Pro or $Xaa_2$ is not Hyp;
  e) determining the melting temperature of each n repeat of step d) relative to the melting temperature of a Gly-Pro-Hyp peptide;
  f) adjusting the melting temperature of each n repeat of step e) with a reference melting temperature for each n repeat of step e), wherein the reference melting temperature comprises:

| $Xaa_1$\$Xaa_2$ | Hyp | Pro | Arg | Met | Ile | Gln |
|---|---|---|---|---|---|---|
| Pro | 47.3 | 45.5 | 47.2 | 42.6 | 41.5 | 41.3 |
| Glu | 42.9 | 41.1 | 40.4 | 38.2 | 37.1 | 37.7 |
| Ala | 41.7 | 37.7 | 38.2 | 37.0 | 35.9 | 35.7 |
| Lys | 41.5 | 39.7 | 39.1 | 36.8 | 35.7 | 38.9 |
| Arg | 40.6 | 38.8 | 38.0 | 35.9 | 34.8 | 34.6 |
| Gln | 40.4 | 38.6 | 39.5 | 35.7 | 34.6 | 34.4 |
| Asp | 40.1 | 38.3 | 37.1 | 35.4 | 34.3 | 34.1 |
| Leu | 39.0 | 37.2 | 36.4 | 34.3 | 33.2 | 35.7 |
| Val | 38.9 | 37.1 | 36.3 | 34.2 | 33.1 | 32.9 |
| Met | 38.6 | 36.8 | 36.0 | 33.9 | 32.8 | 32.6 |
| Ile | 38.4 | 36.6 | 35.8 | 33.7 | 32.6 | 32.4 |
| Asn | 38.3 | 36.5 | 35.7 | 33.6 | 32.5 | 32.3 |
| Ser | 38.0 | 36.2 | 35.4 | 33.3 | 32.2 | 32.0 |
| His | 36.5 | 34.7 | 33.9 | 31.8 | 30.7 | 30.5 |
| Thr | 36.2 | 34.4 | 33.6 | 31.5 | 30.4 | 30.2 |
| Cys | 36.1 | 34.3 | 33.5 | 31.4 | 30.3 | 30.1 |
| Tyr | 34.3 | 32.5 | 31.7 | 29.6 | 28.5 | 28.3 |
| Phe | 33.5 | 31.7 | 30.9 | 28.8 | 27.7 | 27.5 |
| Gly | 33.2 | 31.4 | 30.6 | 28.5 | 27.4 | 27.2 |
| Trp | 31.9 | 30.1 | 29.3 | 27.2 | 26.1 | 25.9 |

| $Xaa_1$\$Xaa_2$ | Ala | Val | Glu | Thr | Cys | Lys |
|---|---|---|---|---|---|---|
| Pro | 40.9 | 40.0 | 39.7 | 39.7 | 37.7 | 36.8 |
| Glu | 34.6 | 35.3 | 35.3 | 35.9 | 33.3 | 35.0 |
| Ala | 32.9 | 34.4 | 34.1 | 34.1 | 32.1 | 30.8 |
| Lys | 35.1 | 34.2 | 35.3 | 33.9 | 31.9 | 31.0 |
| Arg | 34.2 | 33.3 | 33.8 | 33.0 | 31.0 | 29.5 |
| Gln | 34.0 | 33.1 | 32.8 | 32.8 | 30.8 | 32.6 |
| Asp | 31.6 | 32.8 | 32.5 | 32.5 | 30.5 | 30.9 |
| Leu | 31.2 | 31.7 | 31.4 | 31.4 | 29.4 | 31.1 |
| Val | 32.5 | 31.6 | 31.3 | 31.3 | 29.3 | 32.5 |
| Met | 32.2 | 31.3 | 31.0 | 31.0 | 29.0 | 31.7 |
| Ile | 33.9 | 31.1 | 30.8 | 30.8 | 28.8 | 27.9 |
| Asn | 31.9 | 31.0 | 30.7 | 30.7 | 28.7 | 27.8 |
| Ser | 31.6 | 30.7 | 30.4 | 30.4 | 28.4 | 27.5 |
| His | 30.1 | 29.2 | 28.9 | 28.9 | 26.9 | 26.0 |
| Thr | 29.8 | 28.9 | 28.6 | 28.6 | 26.6 | 25.7 |
| Cys | 29.7 | 28.8 | 28.5 | 28.5 | 26.5 | 25.6 |
| Tyr | 27.9 | 27.0 | 26.7 | 26.7 | 24.7 | 23.8 |
| Phe | 24.1 | 26.2 | 25.9 | 25.9 | 23.9 | 23.0 |
| Gly | 26.0 | 25.9 | 25.6 | 25.6 | 23.6 | 26.9 |
| Trp | 25.5 | 24.6 | 24.3 | 24.3 | 22.3 | 21.4 |

-continued

| Xaa₁/Xaa₂ | His | Ser | Asp | Gly | Leu | Asn |
|---|---|---|---|---|---|---|
| Pro | 35.7 | 35.0 | 34.0 | 32.9 | 32.7 | 31.7 |
| Glu | 31.3 | 30.6 | 29.7 | 28.5 | 28.3 | 29.5 |
| Ala | 30.1 | 33.0 | 33.0 | 27.3 | 27.8 | 26.1 |
| Lys | 29.9 | 29.2 | 35.8 | 27.1 | 26.9 | 31.7 |
| Arg | 29.0 | 30.5 | 34.5 | 26.2 | 26.0 | 25.0 |
| Gln | 28.8 | 28.1 | 27.1 | 26.0 | 25.8 | 24.8 |
| Asp | 28.5 | 27.8 | 26.8 | 25.7 | 25.5 | 24.5 |
| Len | 27.4 | 26.7 | 25.7 | 24.6 | 26.9 | 23.4 |
| Val | 27.3 | 26.6 | 25.6 | 24.5 | 24.3 | 23.3 |
| Met | 27.0 | 26.3 | 25.3 | 24.2 | 24.0 | 23.0 |
| Ile | 26.8 | 26.1 | 25.1 | 24.0 | 23.8 | 22.8 |
| Asn | 26.7 | 26.0 | 25.0 | 23.9 | 23.7 | 22.7 |
| Ser | 26.4 | 25.7 | 24.7 | 23.6 | 23.4 | 22.1 |
| His | 24.9 | 24.2 | 23.2 | 22.1 | 21.9 | 20.9 |
| Thr | 24.6 | 23.9 | 22.9 | 21.8 | 21.6 | 20.6 |
| Cys | 24.5 | 23.8 | 22.8 | 21.7 | 21.5 | 20.5 |
| Tyr | 22.7 | 22.0 | 21.0 | 19.9 | 19.7 | 18.7 |
| Phe | 21.9 | 21.2 | 20.2 | 19.1 | 18.9 | 17.9 |
| Gly | 21.6 | 20.9 | 19.9 | 18.8 | 25.3 | 17.6 |
| Trp | 20.3 | 19.6 | 18.6 | 17.5 | 17.3 | 16.3 |

| Xaa₁/Xaa₂ | Tyr | Phe | Trp |
|---|---|---|---|
| Pro | 30.2 | 28.4 | 26.1 |
| Glu | 25.8 | 24.0 | 21.7 |
| Ala | 24.6 | 21.9 | 20.5 |
| Lys | 24.4 | 22.6 | 20.3 |
| Arg | 23.5 | 21.7 | 19.4 |
| Gln | 23.3 | 21.5 | 19.2 |
| Asp | 23.0 | 21.2 | 18.9 |
| Len | 21.9 | 20.1 | 17.8 |
| Val | 21.8 | 20.0 | 17.7 |
| Met | 21.5 | 19.7 | 17.4 |
| Ile | 21.3 | 19.5 | 17.2 |
| Asn | 21.2 | 19.4 | 17.1 |
| Ser | 20.9 | 19.1 | 16.8 |
| His | 19.4 | 17.6 | 15.3 |
| Thr | 19.1 | 17.3 | 15.0 |
| Cys | 19.0 | 17.2 | 14.9 |
| Tyr | 17.2 | 15.4 | 13.1 |
| Phe | 16.4 | 14.6 | 12.3 |
| Gly | 16.1 | 19.7 | 12.0 |
| Trp | 14.8 | 13.0 | 10.7 | g) combining the adjusted melting temperatures of the n repeats of steps f) so that a correction melting temperature is determined for Gly-Xaa₁-Xaa₂ repeats; and h) adjusting the maximum melting temperature of the collagen peptide, collagen-like peptide or triple-helix construct of step c) with the correction melting temperature of g) to determine the thermal stability of the collagen peptide, collagen-like peptide or triple-helix construct; and i) identifying the presence of a stabilizing sequence motif in the collagen peptide, collagen-like peptide or triple-helix construct, wherein the stabilizing sequence motif comprises Lys-Gly-Glu/Asp, and adjusting the melting temperature of step h) for the collagen peptide, collagen-like peptide or triple-helix construct when the stabilizing sequence motif is present.

2. The method of claim 1, wherein the collagen peptide, collagen-like peptide or triple-helix construct is within a protein or collagen domain of a protein.

3. The method of claim 2, wherein a disease-causing mutation is present in the protein.

4. A method for designing a collagen peptide, collagen-like peptide or triple-helix construct with a predetermined thermal stability comprising a) obtaining the primary amino acid sequence of a collagen peptide, collagen-like peptide or triple-helix construct having consecutive repeating units of the tripeptide (Gly-Xaa₁-Xaa₂)$_n$, wherein Xaa₁ and Xaa₂ are any amino acid residue and n is at least 6;

b) identifying the number of consecutive Gly-Xaa₁-Xaa₂ amino acid repeats in the collagen peptide, collagen-like peptide or triple-helix construct by computer inspection of the primary amino acid sequence of the collagen peptide, collagen-like peptide or triple-helix construct;

c) determining the maximum melting temperature of the collagen peptide, collagen-like peptide or triple-helix construct relative to the melting temperature of a (Gly-Pro-Hyp)$_n$ peptide, wherein n corresponds to the number of consecutive Gly-Xaa₁-Xaa₂ amino acid repeats in the collagen peptide, collagen-like peptide or triple-helix construct;

d) identifying Gly-Xaa₁-Xaa₂ amino acid repeats in the collagen peptide, collagen-like peptide or triple-helix construct wherein Xaa₁ is not Pro or Xaa₂ is not Hyp;

e) determining the melting temperature of each n repeat of step d) relative to the melting temperature of a Gly-Pro-Hyp peptide;

f) adjusting the melting temperature of each n repeat of step e) with a reference melting temperature for each n repeat of step e), wherein the reference melting temperature comprises:

| Xaa₁\Xaa₂ | Hyp | Pro | Arg | Met | Ile | Gln |
|---|---|---|---|---|---|---|
| Pro | 47.3 | 45.5 | 47.2 | 42.6 | 41.5 | 41.3 |
| Glu | 42.9 | 41.1 | 40.4 | 38.2 | 37.1 | 37.7 |
| Ala | 41.7 | 37.7 | 38.2 | 37.0 | 35.9 | 35.7 |
| Lys | 41.5 | 39.7 | 39.1 | 36.8 | 35.7 | 38.9 |
| Arg | 40.6 | 38.8 | 38.0 | 35.9 | 34.8 | 34.6 |
| Gln | 40.4 | 38.6 | 39.5 | 35.7 | 34.6 | 34.4 |
| Asp | 40.1 | 38.3 | 37.1 | 35.4 | 34.3 | 34.1 |
| Leu | 39.0 | 37.2 | 36.4 | 34.3 | 33.2 | 35.7 |
| Val | 38.9 | 37.1 | 36.3 | 34.2 | 33.1 | 32.9 |
| Met | 38.6 | 36.8 | 36.0 | 33.9 | 32.8 | 32.6 |
| Ile | 38.4 | 36.6 | 35.8 | 33.7 | 32.6 | 32.4 |
| Asn | 38.3 | 36.5 | 35.7 | 33.6 | 32.5 | 32.3 |
| Ser | 38.0 | 36.2 | 35.4 | 33.3 | 32.2 | 32.0 |
| His | 36.5 | 34.7 | 33.9 | 31.8 | 30.7 | 30.5 |
| Thr | 36.2 | 34.4 | 33.6 | 31.5 | 30.4 | 30.2 |
| Cys | 36.1 | 34.3 | 33.5 | 31.4 | 30.3 | 30.1 |
| Tyr | 34.3 | 32.5 | 31.7 | 29.6 | 28.5 | 28.3 |
| Phe | 33.5 | 31.7 | 30.9 | 28.8 | 27.7 | 27.5 |
| Gly | 33.2 | 31.4 | 30.6 | 28.5 | 27.4 | 27.2 |
| Trp | 31.9 | 30.1 | 29.3 | 27.2 | 26.1 | 25.9 |

| Xaa₁\Xaa₂ | Ala | Val | Glu | Thr | Cys | Lys |
|---|---|---|---|---|---|---|
| Pro | 40.9 | 40.0 | 39.7 | 39.7 | 37.7 | 36.8 |
| Glu | 34.6 | 35.3 | 35.3 | 35.9 | 33.3 | 35.0 |
| Ala | 32.9 | 34.4 | 34.1 | 34.1 | 32.1 | 30.8 |
| Lys | 35.1 | 34.2 | 35.3 | 33.9 | 31.9 | 31.0 |
| Arg | 34.2 | 33.3 | 33.8 | 33.0 | 31.0 | 29.5 |
| Gln | 34.0 | 33.1 | 32.8 | 32.8 | 30.8 | 32.6 |
| Asp | 31.6 | 32.8 | 32.5 | 32.5 | 30.5 | 30.9 |
| Leu | 31.2 | 31.7 | 31.4 | 31.4 | 29.4 | 31.1 |
| Val | 32.5 | 31.6 | 31.3 | 31.3 | 29.3 | 32.5 |
| Met | 32.2 | 31.3 | 31.0 | 31.0 | 29.0 | 31.7 |
| Ile | 33.9 | 31.1 | 30.8 | 30.8 | 28.8 | 27.9 |
| Asn | 31.9 | 31.0 | 30.7 | 30.7 | 28.7 | 27.8 |
| Ser | 31.6 | 30.7 | 30.4 | 30.4 | 28.4 | 27.5 |
| His | 30.1 | 29.2 | 28.9 | 28.9 | 26.9 | 26.0 |
| Thr | 29.8 | 28.9 | 28.6 | 28.6 | 26.6 | 25.7 |
| Cys | 29.7 | 28.8 | 28.5 | 28.5 | 26.5 | 25.6 |
| Tyr | 27.9 | 27.0 | 26.7 | 26.7 | 24.7 | 23.8 |
| Phe | 24.1 | 26.2 | 25.9 | 25.9 | 23.9 | 23.0 |
| Gly | 26.0 | 25.9 | 25.6 | 25.6 | 23.6 | 26.9 |
| Trp | 25.5 | 24.6 | 24.3 | 24.3 | 22.3 | 21.4 |

| Xaa₁/Xaa₂ | His | Ser | Asp | Gly | Leu | Asn |
|---|---|---|---|---|---|---|
| Pro | 35.7 | 35.0 | 34.0 | 32.9 | 32.7 | 31.7 |
| Glu | 31.3 | 30.6 | 29.7 | 28.5 | 28.3 | 29.5 |
| Ala | 30.1 | 33.0 | 33.0 | 27.3 | 27.8 | 26.1 |

-continued

| | | | | | | |
|---|---|---|---|---|---|---|
| Lys | 29.9 | 29.2 | 35.8 | 27.1 | 26.9 | 31.7 |
| Arg | 29.0 | 30.5 | 34.5 | 26.2 | 26.0 | 25.0 |
| Gln | 28.8 | 28.1 | 27.1 | 26.0 | 25.8 | 24.8 |
| Asp | 28.5 | 27.8 | 26.8 | 25.7 | 25.5 | 24.5 |
| Len | 27.4 | 26.7 | 25.7 | 24.6 | 26.9 | 23.4 |
| Val | 27.3 | 26.6 | 25.6 | 24.5 | 24.3 | 23.3 |
| Met | 27.0 | 26.3 | 25.3 | 24.2 | 24.0 | 23.0 |
| Ile | 26.8 | 26.1 | 25.1 | 24.0 | 23.8 | 22.8 |
| Asn | 26.7 | 26.0 | 25.0 | 23.9 | 23.7 | 22.7 |
| Ser | 26.4 | 25.7 | 24.7 | 23.6 | 23.4 | 22.1 |
| His | 24.9 | 24.2 | 23.2 | 22.1 | 21.9 | 20.9 |
| Thr | 24.6 | 23.9 | 22.9 | 21.8 | 21.6 | 20.6 |
| Cys | 24.5 | 23.8 | 22.8 | 21.7 | 21.5 | 20.5 |
| Tyr | 22.7 | 22.0 | 21.0 | 19.9 | 19.7 | 18.7 |
| Phe | 21.9 | 21.2 | 20.2 | 19.1 | 18.9 | 17.9 |
| Gly | 21.6 | 20.9 | 19.9 | 18.8 | 25.3 | 17.6 |
| Trp | 20.3 | 19.6 | 18.6 | 17.5 | 17.3 | 16.3 |

| $Xaa_1/Xaa_2$ | Tyr | Phe | Trp |
|---|---|---|---|
| Pro | 30.2 | 28.4 | 26.1 |
| Glu | 25.8 | 24.0 | 21.7 |
| Ala | 24.6 | 21.9 | 20.5 |
| Lys | 24.4 | 22.6 | 20.3 |
| Arg | 23.5 | 21.7 | 19.4 |
| Gln | 23.3 | 21.5 | 19.2 |
| Asp | 23.0 | 21.2 | 18.9 |
| Len | 21.9 | 20.1 | 17.8 |
| Val | 21.8 | 20.0 | 17.7 |
| Met | 21.5 | 19.7 | 17.4 |
| Ile | 21.3 | 19.5 | 17.2 |
| Asn | 21.2 | 19.4 | 17.1 |
| Ser | 20.9 | 19.1 | 16.8 |
| His | 19.4 | 17.6 | 15.3 |
| Thr | 19.1 | 17.3 | 15.0 |
| Cys | 19.0 | 17.2 | 14.9 |
| Tyr | 17.2 | 15.4 | 13.1 |
| Phe | 16.4 | 14.6 | 12.3 |
| Gly | 16.1 | 19.7 | 12.0 |
| Trp | 14.8 | 13.0 | 10.7 | g) combining the adjusted melting temperatures of the n repeats of steps f) so that a correction melting temperature is determined for Gly-$Xaa_1$-$Xaa_2$ repeats;

h) adjusting the maximum melting temperature of the collagen peptide, collagen-like peptide or triple-helix construct of step c) with the correction melting temperature of g);

i) identifying the presence of a stabilizing sequence motif in the collagen peptide, collagen-like peptide or triple-helix construct, wherein the stabilizing sequence motif comprises Lys-Gly-Glu/Asp, and adjusting the melting temperature of step h) for the collagen peptide, collagen-like peptide or triple-helix construct when the stabilizing sequence motif is present thereby determining the thermal stability of the collagen peptide, collagen-like peptide or triple-helix construct; and j) modifying the primary amino acid sequence of the collagen peptide, collagen-like peptide or triple-helix construct to obtain a collagen peptide, collagen-like peptide or triple-helix construct with a predetermined thermal stability.

* * * * *

UNITED STATES PATENT AND TRADEMARK OFFICE
CERTIFICATE OF CORRECTION

| | |
|---|---|
| PATENT NO. | : 8,280,710 B2 |
| APPLICATION NO. | : 11/814607 |
| DATED | : October 2, 2012 |
| INVENTOR(S) | : Anton V. Persikov |

It is certified that error appears in the above-identified patent and that said Letters Patent is hereby corrected as shown below:

In the Claims:

Claim 1
At column 75, line 10, please delete "Len"
At column 75, line 10, please insert --Leu--

Claim 1
At column 75, line 14, please delete "22.1"
At column 75, line 14, please insert --22.4--

Claim 1
At column 75, line 28, please delete "Len"
At column 75, line 28, please insert --Leu--

Claim 4
At column 77, line 6, please delete "Len"
At column 77, line 6, please insert --Leu--

Claim 4
At column 77, line 10, please delete "22.1"
At column 77, line 10, please insert --22.4--

Claim 4
At column 77, line 24, please delete "Len"
At column 77, line 24, please insert --Leu--

Signed and Sealed this
Seventh Day of May, 2013

Teresa Stanek Rea
*Acting Director of the United States Patent and Trademark Office*

SEQUENCE LISTING

```
<160> NUMBER OF SEQ ID NOS: 55

<210> SEQ ID NO 1
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 1

Gly Pro Pro Gly Pro Pro Gly Pro Pro Gly Pro Pro Gly Pro Pro Gly
1               5                   10                  15

Pro Pro Gly Pro Pro Gly Pro Pro
            20

<210> SEQ ID NO 2
<211> LENGTH: 6
<212> TYPE: PRT
<213> ORGANISM: Artificial Sequence
<220> FEATURE:
<223> OTHER INFORMATION: Consensus peptide
<220> FEATURE:
<221> NAME/KEY: MISC_FEATURE
```

```
<222> LOCATION: (2)..(2)
<223> OTHER INFORMATION: Xaa denotes any amino acid residue
<220> FEATURE:
<221> NAME/KEY: MISC_FEATURE
<222> LOCATION: (6)..(6)
<223> OTHER INFORMATION: Xaa denotes any amino acid residue

<400> SEQUENCE: 2

Gly Xaa Leu Gly Leu Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Consensus peptide
<220> FEATURE:
<221> NAME/KEY: MISC_FEATURE
<222> LOCATION: (3)..(3)
<223> OTHER INFORMATION: Xaa denotes any amino acid residue
<220> FEATURE:
<221> NAME/KEY: MISC_FEATURE
<222> LOCATION: (6)..(6)
<223> OTHER INFORMATION: Xaa denotes any amino acid residue

<400> SEQUENCE: 3

Gly Leu Xaa Gly Leu Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Consensus peptide
<220> FEATURE:
<221> NAME/KEY: MISC_FEATURE
<222> LOCATION: (2)..(2)
<223> OTHER INFORMATION: Xaa denotes any amino acid residue
<220> FEATURE:
<221> NAME/KEY: MISC_FEATURE
<222> LOCATION: (6)..(6)
<223> OTHER INFORMATION: Xaa denotes any amino acid residue

<400> SEQUENCE: 4

Gly Xaa Lys Gly Asp Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Consensus peptide
<220> FEATURE:
<221> NAME/KEY: MISC_FEATURE
<222> LOCATION: (2)..(2)
<223> OTHER INFORMATION: Xaa denotes any amino acid residue
<220> FEATURE:
<221> NAME/KEY: MISC_FEATURE
<222> LOCATION: (6)..(6)
<223> OTHER INFORMATION: Xaa denotes any amino acid residue

<400> SEQUENCE: 5

Gly Xaa Lys Gly Glu Xaa
1               5

<210> SEQ ID NO 6
<211> LENGTH: 6
<212> TYPE: PRT
<213> ORGANISM: Artificial Sequence
```

```
<220> FEATURE:
<223> OTHER INFORMATION: Consensus peptide
<220> FEATURE:
<221> NAME/KEY: MISC_FEATURE
<222> LOCATION: (3)..(3)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes any amino acid residue

<400> SEQUENCE: 6

Gly Glu Xaa Gly Xaa Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Consensus peptide
<220> FEATURE:
<221> NAME/KEY: MISC_FEATURE
<222> LOCATION: (2)..(2)
<223> OTHER INFORMATION: Xaa denotes any amino acid residue
<220> FEATURE:
<221> NAME/KEY: MISC_FEATURE
<222> LOCATION: (5)..(5)
<223> OTHER INFORMATION: Xaa denotes any amino acid residue

<400> SEQUENCE: 7

Gly Xaa Lys Gly Xaa Glu
1               5

<210> SEQ ID NO 8
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp

<400> SEQUENCE: 8

Pro Pro Gly Pro Pro Gly Pro Pro Gly Pro Pro Gly Pro Pro Gly Pro
1               5                   10                  15

Pro Gly Pro Pro Gly
            20
```

```
<210> SEQ ID NO 9
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp

<400> SEQUENCE: 9

Pro Pro Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 10
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (24)..(24)
<223> OTHER INFORMATION: 4Hyp
```

-continued

```
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 10

Gly Pro Pro Gly Pro Pro Gly Pro Pro Gly Ala Lys Gly Asp Ala Gly
1               5                   10                  15

Pro Pro Gly Pro Ala Gly Pro Pro Gly Pro Pro Gly Pro Pro Gly Tyr
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 11

Gly Pro Ala Gly Pro Ala Gly Pro Val Gly Pro Ala Gly Ala Arg Gly
1               5                   10                  15

Pro Ala Gly Pro Pro Gly Pro Pro Gly Pro Pro Gly Pro Pro Gly Val
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
```

```
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 12

Gly Pro Pro Gly Pro Pro Gly Pro Pro Gly Pro Pro Gly Pro Ala Gly
1               5                   10                  15

Pro Ala Gly Pro Val Gly Pro Ala Gly Ala Arg Gly Pro Ala Gly Val
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 13

Gly Pro Ala Gly Pro Ala Gly Pro Val Gly Pro Ala Gly Ala Arg Gly
1               5                   10                  15

Pro Ala Gly Pro Pro Gly Pro Pro Gly Ala Pro Gly Pro Pro Gly Val
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
```

```
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 14

Gly Pro Ala Gly Pro Ala Gly Pro Val Gly Pro Ala Gly Ala Arg Gly
1               5                   10                  15

Pro Ala Gly Pro Pro Gly Pro Ala Gly Pro Pro Gly Pro Pro Gly Val
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 15

Gly Pro Ala Gly Pro Ala Gly Pro Val Gly Pro Ala Gly Ala Arg Gly
1               5                   10                  15

Pro Ala Gly Pro Pro Gly Pro Pro Gly Pro Pro Gly Pro Pro Gly Tyr
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION
```

-continued

```
<400> SEQUENCE: 16

Gly Ala Arg Gly Pro Ala Gly Pro Gln Gly Pro Arg Gly Asp Lys Gly
1               5                   10                  15

Glu Thr Gly Pro Pro Gly Pro Pro Gly Pro Pro Gly Pro Pro Gly Val
                20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 17

Gly Phe Pro Gly Ala Ala Gly Arg Thr Gly Pro Pro Gly Pro Ser Gly
1               5                   10                  15

Ile Ser Gly Pro Pro Gly Pro Pro Gly Pro Pro Gly Pro Pro Gly Val
                20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
```

```
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: HYDROXYLATION

<400> SEQUENCE: 18

Gly Ser Pro Gly Ala Gln Gly Leu Gln Gly Pro Arg Gly Leu Pro Gly
1               5                   10                  15

Thr Pro Gly Pro Pro Gly Pro Pro Gly Pro Pro Gly Pro Pro Gly Val
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 19

Gly Gly Lys Gly Asp Ala Gly Ala Pro Gly Glu Arg Gly Pro Pro Gly
1               5                   10                  15

Leu Ala Gly Pro Pro Gly Pro Pro Gly Pro Pro Gly Pro Pro Gly Val
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 20

Gly Asp Ala Gly Ala Pro Gly Glu Arg Gly Pro Pro Gly Leu Ala Gly
1               5                   10                  15

Ala Pro Gly Pro Pro Gly Pro Pro Gly Pro Pro Gly Pro Pro Gly Val
                20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
```

-continued

```
<400> SEQUENCE: 21

Gly Ala Pro Gly Glu Arg Gly Pro Pro Gly Leu Ala Gly Ala Pro Gly
1               5                   10                  15

Leu Arg Gly Pro Pro Gly Pro Pro Gly Pro Pro Gly Pro Pro Gly Val
                20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 22

Gly Glu Arg Gly Pro Pro Gly Leu Ala Gly Ala Pro Gly Leu Arg Gly
1               5                   10                  15

Gly Ala Gly Pro Pro Gly Pro Pro Gly Pro Pro Gly Pro Pro Gly Val
                20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
```

```
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 23

Gly Pro Pro Gly Leu Ala Gly Ala Pro Gly Leu Arg Gly Gly Ala Gly
1               5                   10                  15

Pro Pro Gly Pro Pro Gly Pro Pro Gly Pro Pro Gly Pro Pro Gly Val
                20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 24

Gly Leu Ala Gly Ala Pro Gly Leu Arg Gly Gly Ala Gly Pro Pro Gly
1               5                   10                  15

Pro Glu Gly Pro Pro Gly Pro Pro Gly Pro Pro Gly Pro Pro Gly Val
                20                  25                  30

<210> SEQ ID NO 25
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<220> FEATURE:
```

```
<221> NAME/KEY: MOD_RES
<222> LOCATION: (6)..(6)
<220> FEATURE:
<221> NAME/KEY: MOD_RES
<222> LOCATION: (24)..(24)
<220> FEATURE:
<221> NAME/KEY: MOD_RES
<222> LOCATION: (27)..(27)
<220> FEATURE:
<221> NAME/KEY: MOD_RES
<222> LOCATION: (27)..(27)
<220> FEATURE:
<221> NAME/KEY: MOD_RES
<222> LOCATION: (30)..(30)
<220> FEATURE:
<221> NAME/KEY: MOD_RES
<222> LOCATION: (33)..(33)
<220> FEATURE:
<221> NAME/KEY: MOD_RES
<222> LOCATION: (35)..(35)
<223> OTHER INFORMATION: AMIDATION

<400> SEQUENCE: 25

Gly Pro Pro Gly Ala Pro Gly Pro Leu Gly Ile Ala Gly Ile Thr Gly
1               5                   10                  15

Ala Arg Gly Leu Ala Gly Pro Pro Gly Pro Pro Gly Pro Pro Gly Pro
            20                  25                  30

Pro Gly Gly
        35

<210> SEQ ID NO 26
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp

<400> SEQUENCE: 26

Pro Pro Gly Pro Pro Gly Pro Pro Gly Ile Thr Gly Ala Arg Gly Leu
1               5                   10                  15

Ala Gly Pro Pro Gly Pro Pro Gly Pro Pro Gly Pro Pro Gly
            20                  25                  30

<210> SEQ ID NO 27
<211> LENGTH: 32
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 27

Gly Pro Arg Gly Asn Arg Gly Glu Arg Gly Ser Glu Gly Ser Pro Gly
1               5                   10                  15

His Pro Gly Gln Pro Gly Pro Pro Gly Pro Pro Gly Ala Pro Gly Val
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
```

```
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 28

Gly Leu Ala Gly Glu Pro Gly Lys Pro Gly Ile Pro Gly Leu Pro Gly
1               5                   10                  15

Arg Ala Gly Pro Pro Gly Pro Pro Gly Pro Pro Gly Pro Pro Gly Val
                20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 29

Gly Glu Arg Gly Glu Arg Gly Glu Lys Gly Glu Arg Gly Glu Gln Gly
1               5                   10                  15

Arg Asp Gly Pro Pro Gly Pro Pro Gly Pro Pro Gly Pro Pro Gly Val
                20                  25                  30

<210> SEQ ID NO 30
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
```

```
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (26)..(26)
<223> OTHER INFORMATION: AMIDATION

<400> SEQUENCE: 30

Gly Pro Pro Gly Pro Pro Gly Pro Pro Gly Lys Arg Gly Lys Pro Gly
 1               5                  10                  15

Pro Pro Gly Pro Pro Gly Pro Pro Gly Gly
            20                  25

<210> SEQ ID NO 31
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (26)..(26)
<223> OTHER INFORMATION: AMIDATION

<400> SEQUENCE: 31

Gly Pro Pro Gly Pro Pro Gly Arg Pro Gly Lys Arg Gly Lys Pro Gly
```

```
                  1               5              10              15
Pro Pro Gly Pro Pro Gly Pro Pro Gly Gly
                 20              25

<210> SEQ ID NO 32
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (26)..(26)
<223> OTHER INFORMATION: AMIDATION

<400> SEQUENCE: 32

Gly Pro Pro Gly Pro Pro Gly Arg Pro Gly Lys Arg Gly Lys Gln Gly
1               5                  10                  15
Pro Pro Gly Pro Pro Gly Pro Pro Gly Gly
                 20              25

<210> SEQ ID NO 33
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
```

```
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (26)..(26)
<223> OTHER INFORMATION: AMIDATION

<400> SEQUENCE: 33

Gly Pro Pro Gly Pro Pro Gly Arg Gln Gly Lys Arg Gly Lys Pro Gly
1               5                   10                  15

Pro Pro Gly Pro Pro Gly Pro Pro Gly Gly
            20                  25

<210> SEQ ID NO 34
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (26)..(26)
<223> OTHER INFORMATION: AMIDATION

<400> SEQUENCE: 34

Gly Pro Pro Gly Pro Pro Gly Arg Pro Gly Lys Arg Gly Lys Gln Gly
1               5                   10                  15

Gln Lys Gly Pro Pro Gly Pro Pro Gly Gly
            20                  25

<210> SEQ ID NO 35
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
```

```
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (26)..(26)
<223> OTHER INFORMATION: AMIDATION

<400> SEQUENCE: 35

Gly Pro Pro Gly Pro Pro Gly Pro Pro Gly Arg Lys Gly Arg Pro Gly
1               5                   10                  15

Pro Pro Gly Pro Pro Gly Pro Pro Gly Gly
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (26)..(26)
<223> OTHER INFORMATION: AMIDATION
```

-continued

```
<400> SEQUENCE: 36

Gly Pro Pro Gly Pro Pro Gly Arg Pro Gly Arg Lys Gly Arg Pro Gly
1               5                   10                  15
Pro Pro Gly Pro Pro Gly Pro Pro Gly Gly
            20                  25

<210> SEQ ID NO 37
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (30)..(30)
<223> OTHER INFORMATION: AMIDATION

<400> SEQUENCE: 37

Pro Pro Gly Arg Pro Gly Arg Lys Gly Arg Pro Gly Val Arg Gly Pro
1               5                   10                  15
Arg Gly Pro Pro Gly Pro Pro Gly Pro Pro Gly Pro Pro Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (20)..(20)
<223> OTHER INFORMATION: 4Hyp
```

```
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (30)..(30)
<223> OTHER INFORMATION: AMIDATION

<400> SEQUENCE: 38

Pro Pro Gly Arg Pro Gly Ala Ala Gly Ala Pro Gly Val Arg Gly Pro
1               5                   10                  15

Arg Gly Pro Pro Gly Pro Pro Gly Pro Gly Pro Pro Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (30)..(30)
<223> OTHER INFORMATION: AMIDATION

<400> SEQUENCE: 39

Pro Pro Gly Ala Pro Gly Arg Lys Gly Arg Pro Gly Val Ala Gly Pro
1               5                   10                  15

Ala Gly Pro Pro Gly Pro Pro Gly Pro Gly Pro Pro Gly
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (30)..(30)
<223> OTHER INFORMATION: AMIDATION

<400> SEQUENCE: 40

Pro Pro Gly Arg Pro Gly Lys Arg Gly Lys Thr Gly Leu Lys Gly Asp
1               5                   10                  15

Ile Gly Pro Pro Gly Pro Pro Gly Pro Gly Pro Pro Gly
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (30)..(30)
<223> OTHER INFORMATION: AMIDATION

<400> SEQUENCE: 41

Pro Pro Gly Leu Pro Gly Met Leu Gly Gln Lys Gly Glu Met Gly Pro
1               5                   10                  15

Lys Gly Pro Pro Gly Pro Pro Gly Pro Pro Gly Pro Pro Gly
            20                  25                  30
```

```
<210> SEQ ID NO 42
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (30)..(30)
<223> OTHER INFORMATION: AMIDATION

<400> SEQUENCE: 42

Pro Pro Gly Arg Pro Gly Lys Arg Gly Lys Pro Gly Val Arg Gly Pro
1               5                   10                  15

Arg Gly Pro Pro Gly Pro Pro Gly Pro Pro Gly Pro Pro Gly
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
```

```
-continued

<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (31)..(31)
<223> OTHER INFORMATION: AMIDATION

<400> SEQUENCE: 43

Gly Pro Pro Gly Pro Pro Gly Arg Pro Gly Arg Lys Gly Arg Pro Gly
1               5                   10                  15

Pro Pro Gly Pro Pro Gly Pro Pro Gly Pro Pro Gly Pro Pro Gly
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (31)..(31)
<223> OTHER INFORMATION: AMIDATION

<400> SEQUENCE: 44

Gly Pro Pro Gly Pro Pro Gly Arg Pro Gly Lys Arg Gly Lys Gln Gly
1               5                   10                  15

Gln Lys Gly Pro Pro Gly Pro Pro Gly Pro Pro Gly Pro Pro Gly
            20                  25                  30
```

```
<210> SEQ ID NO 45
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp

<400> SEQUENCE: 45

Pro Pro Gly Pro Pro Gly Pro Pro Gly Pro Lys Gly Gln Lys Gly Glu
1               5                   10                  15

Lys Gly Pro Pro Gly Pro Pro Gly Pro Pro Gly Pro Pro Gly
                20                  25                  30

<210> SEQ ID NO 46
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
```

```
<220> FEATURE:
<221> NAME/KEY: MOD_RES
<222> LOCATION: (35)..(35)
<223> OTHER INFORMATION: AMIDATION

<400> SEQUENCE: 46

Gly Ile Asn Gly Phe Pro Gly Lys Asp Gly Arg Asp Gly Thr Lys Gly
1               5                   10                  15

Glu Lys Gly Glu Pro Gly Pro Gly Pro Pro Gly Pro Pro Gly Pro Pro
            20                  25                  30

Pro Gly Gly
        35

<210> SEQ ID NO 47
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 47

Gly Phe Pro Gly Lys Asp Gly Arg Asp Gly Thr Lys Gly Glu Lys Gly
1               5                   10                  15

Glu Pro Gly Pro Pro Gly Pro Pro Gly Pro Pro Gly Pro Pro Gly Tyr
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
```

```
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 48

Gly Pro Pro Gly Arg Pro Gly Arg Arg Gly Arg Pro Gly Leu Lys Gly
1               5                   10                  15

Glu Gln Gly Pro Pro Gly Pro Pro Gly Pro Pro Gly Pro Pro Gly Tyr
                20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (32)..(32)
<223> OTHER INFORMATION: AMIDATION

<400> SEQUENCE: 49

Gly Pro Pro Gly Ile Arg Gly Pro Lys Gly Gln Lys Gly Glu Pro Gly
1               5                   10                  15

Leu Pro Gly Pro Pro Gly Pro Pro Gly Pro Pro Gly Pro Pro Gly Tyr
                20                  25                  30
```

```
<210> SEQ ID NO 50
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 50

Gly Pro Ser Gly Pro Arg Gly Leu Pro Gly Pro Pro Gly Ala Pro Gly
1               5                   10                  15

Pro Gln Gly Phe Gln Gly Pro Pro Gly Glu Pro Gly Glu Pro Gly Ala
            20                  25                  30

Ser Gly Pro Met
        35

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide

<400> SEQUENCE: 51

Gly Glu Arg Gly Glu Lys Gly Glu Arg Gly Glu Gln
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Gly Pro Arg Gly Asp Lys Gly Glu Thr
1               5

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (15)..(15)
<223> OTHER INFORMATION: 4Hyp
```

```
<400> SEQUENCE: 53

Gly Lys Asp Gly Arg Asp Gly Thr Lys Gly Glu Lys Gly Glu Pro
1               5                   10                  15

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Gly Pro Lys Gly Gln Lys Gly Glu Lys
1               5

<210> SEQ ID NO 55
<211> LENGTH: 4
<212> TYPE: PRT
<213> ORGANISM: Artificial Sequence
<220> FEATURE:
<223> OTHER INFORMATION: Synthetic peptide

<400> SEQUENCE: 55

Lys Gly His Arg
1
```